(12) United States Patent
Gron et al.

(10) Patent No.: US 7,977,313 B2
(45) Date of Patent: Jul. 12, 2011

(54) METHODS AND COMPOSITIONS FOR PROMOTING LOCALIZATION OF PHARMACEUTICALLY ACTIVE AGENTS TO BONE

(75) Inventors: Hanne Gron, Durham, NC (US); David Duffin, Raleigh, NC (US); Doug Buechter, Chester Springs, PA (US); Elliott Gruskin, Malvern, PA (US); Michael Lehmicke, West Chester, PA (US)

(73) Assignees: Affinergy, Inc., Durham, NC (US); Synthes USA, LLC, West Chester, PA (US)

( * ) Notice: Subject to any disclaimer, the term of this patent is extended or adjusted under 35 U.S.C. 154(b) by 485 days.

(21) Appl. No.: 12/107,098

(22) Filed: Apr. 22, 2008

(65) Prior Publication Data
US 2008/0268015 A1    Oct. 30, 2008

Related U.S. Application Data

(60) Provisional application No. 60/914,341, filed on Apr. 27, 2007.

(51) Int. Cl.
*A61K 38/00* (2006.01)
(52) U.S. Cl. ...................................................... 514/16.7

(58) Field of Classification Search ........................ None
See application file for complete search history.

(56) References Cited

U.S. PATENT DOCUMENTS

| | | | |
|---|---|---|---|
| 7,208,011 | B2 | 4/2007 | Shanley et al. |
| 7,238,669 | B2 | 7/2007 | Bishop-Hurley et al. |
| 2002/0012652 | A1 | 1/2002 | Levy |
| 2003/0203038 | A1 | 10/2003 | Vail |
| 2005/0085623 | A1 | 4/2005 | Balian |
| 2005/0187162 | A1 | 8/2005 | Dhanaraj |
| 2005/0208095 | A1 | 9/2005 | Hunter |
| 2006/0123505 | A1 | 6/2006 | Kikuchi et al. |
| 2006/0233747 | A1 | 10/2006 | Kochendoerfer |
| 2007/0104758 | A1 | 5/2007 | Hamilton et al. |
| 2007/0160644 | A1 | 7/2007 | Kenan et al. |

OTHER PUBLICATIONS

Written Opinion for the International Searching Authority for PCT/US 08/80321, Mar. 17, 2009.
Written Opinion of the International Searching Authority for PCT/US08/71825, Oct. 31, 2008.
Written Opinion of the International Searching Authority for PCT/US08/61200, Sep. 29, 2008.

*Primary Examiner* — Christina Bradley
(74) *Attorney, Agent, or Firm* — Woodcock Washburn LLP

(57) ABSTRACT

Compositions are provided comprising a family of peptides having binding specificity for bone, and their use to produce coating compositions. The coating compositions are used to deliver a pharmaceutically active agent to bone, and are used in methods related to bone implants, bone repair, and bone-related diseases.

20 Claims, No Drawings

METHODS AND COMPOSITIONS FOR PROMOTING LOCALIZATION OF PHARMACEUTICALLY ACTIVE AGENTS TO BONE

CROSS REFERENCE TO RELATED APPLICATIONS

This is a nonprovisional application which claims priority benefit of U.S. Provisional Application No. 60/914,341, filed 27 Apr. 2007, which is hereby incorporated by reference herein.

FIELD OF THE INVENTION

Inventive subject matter described herein relates to compositions and methods for targeting pharmaceutically active agents to bone. More particularly, inventive subject matter is directed to bone-tropic peptides usable in compositions and methods related to bone implants, bone repair, and bone-related diseases.

BACKGROUND OF THE INVENTION

In vertebrates, bone is a connective tissue formed by collagen fibers embedded in a calcium-based crystalline structure of hydroxyapatite. Bone integrity is compromised by trauma, infection, carcinoma, degenerative diseases, or by surgical procedures.

Demineralized bone matrix, DBM, has been widely used in clinical practice as bone implant material. However, DBM has a relatively low ability to be osteoinductive. The DBM's lack of ability to induce osteoinduction is viewed as a factor limiting use of the material as an alternative form of bone.

SUMMARY OF THE INVENTION

One embodiment according to the invention includes a coating composition. The coating composition includes at least one binding domain that binds specifically to bone, and at least one binding domain that binds specifically to a pharmaceutically active agent. The at least one binding domain that binds specifically to bone is coupled to the at least one binding domain that binds specifically to a pharmaceutically active agent. The one binding domain that binds specifically to bone comprises a peptide. The peptide comprises from about 5 amino acids to about 50 amino acids; and a domain or motif comprised of 3 or more large aromatic amino acid residues within a sequence comprising contiguous amino acids in a range of from within the first 5 to first 10 amino acids from an N-terminal end of the peptide. The peptide also has binding specificity for bone. The peptide lacks a collagen sequence cell-binding domain characterized by the sequence Gly-Ile-Ala. The at least one binding domain that binds specifically to a pharmaceutically active agent comprises a peptide comprising an amino acid sequence having from about 3 amino acids to about 50 amino acids, and has binding specificity for a pharmaceutically active agent.

Another embodiment according to the invention includes a composition of the formula:

$X_1$-J-$X_2$-P;

wherein $X_1$ comprises a peptide: (i) comprising from about 5 amino acids to about 50 amino acids; (ii) comprising a domain or motif comprised of 3 or more large aromatic amino acid residues selected from the group consisting of tyrosine, phenylalanine, tryptophan, and a combination thereof, within a sequence comprising the contiguous amino acids in the range of from within the first 5 to first 10 amino acids from an N-terminal end of the peptide; (iii) having binding specificity for bone; and (iv) lacking a collagen-derived cell-binding domain characterized by the sequence Gly-Ile-Ala.

J is absent, or is a linker.

$X_2$ is absent, or comprises a peptide comprising an amino acid sequence having from about 3 amino acids to about 50 amino acids, and having binding specificity for a pharmaceutically active agent.

P is absent, or comprises a pharmaceutically active agent wherein if any one or more of $X_2$ and P are absent, $X_1$ comprises a peptide comprising an amino acid sequence having the sequence of any one of SEQ ID NOs:1-45, or an amino acid sequence having 95% identity with a sequence of any one of SEQ ID NOs:1-45.

Another embodiment comprises a bone-tropic peptide. The bone-tropic peptide comprises: three or more aromatic amino acid residues comprising one or more of Phe, Try, and Tyr, within an amino acid sequence comprising five contiguous amino acids, wherein the bone-tropic peptides have binding specificity for bone, and are free of a sequence for binding collagen characterized by the sequence Gly-Ile-Ala.

Another embodiment includes a delivery system, for delivering pharmaceutically active agents to bone or a bone implant, comprising: a peptide comprising a first binding domain that binds to bone wherein the first binding domain comprises one or more of peptides having SEQ ID NOs. 1-45; the peptide comprising a second binding domain that binds to a pharmaceutically active agent; and a contactor system for contacting the peptide to bone or implant comprising bone.

DETAILED DESCRIPTION OF THE INVENTION

Numerous embodiments are described in this patent application, and are presented for illustrative purposes only. The described embodiments are not, and are not intended to be, limiting in any sense. The presently disclosed invention(s) are widely applicable to numerous embodiments, as is readily apparent from the disclosure. One of ordinary skill in the art will recognize that the disclosed invention(s) may be practiced with various modifications and alterations, such as structural and chemical modifications. Although particular features of the disclosed invention(s) may be described with reference to one or more particular embodiments and/or drawings, it should be understood that such features are not limited to usage in the one or more particular embodiments or drawings with reference to which they are described, unless expressly specified otherwise.

The present disclosure is neither a literal description of all embodiments nor a listing of features of the invention that must be present in all embodiments.

Neither the Title (set forth at the beginning of the first page of this patent application) nor the Abstract (set forth at the end of this patent application) is to be taken as limiting in any way as to the scope of the disclosed invention(s).

Inventive subject matter includes methods and compositions for targeting bone using one or more peptides having binding specificity for bone (also termed herein as "bone-tropic peptides"). For some embodiments, the binding specificity is for Type I collagen found in bone. It is unexpected that one or more of these peptides may, by themselves, bind to bone and serve as a pharmaceutically active agent in promoting one or more of osteoinduction, osteoconduction, and/or osteogenesis. Additionally, some peptide embodiments are coupled to one or more pharmaceutically acceptable agents, forming coating composition embodiments of the invention, for delivering and localizing the one or more pharmaceutically active agents to bone.

In one embodiment, coating compositions include a peptide. For some embodiments, coating compositions are applied to bone, forming a coating on the bone surface. For other embodiments, coating compositions are applied to bone implants. The coated bone surface or implant surface recruits and/or promotes attachment of endogenously-produced pharmaceutically active agents such as those produced by an individual receiving the coated bone or coated bone implant. The coating composition embodiments promote one or more of osteoinduction, osteoconduction, and/or osteogenesis.

Inventive subject matter also includes a family of peptides that share structure and function. The peptides include amino acid sequences rich in large aromatic amino acid residues that include one or more of Phe, Trp, Tyr. The peptides have binding specificity for bone. This family of peptides lacks the collagen sequence cell-binding domain, such as Gly-Ile-Ala, that is further described in U.S. Pat. No. 6,818,620. This family of peptides is characterized by its own unique domain (contributing to bone binding or bone tropism) that includes 3 or more large aromatic amino acids residues within a sequence that includes 5 contiguous amino acids of the amino acid sequence of the peptide. Also included in this embodiment of the invention, are nucleotide sequences and vectors encoding these peptides. A list of peptide embodiments within the family, along with their amino acid sequences, is illustrated in Table 1.

TABLE 1

| SEQ ID NO: | Bone tropic peptides Amino acid sequence (single letter code) |
|---|---|
| 1 | FYSIFFPQMGGSM |
| 2 | FSGWFLPWEGRSE |
| 3 | FYWPSFNSGNSLW |
| 4 | FSWFSYPSQLWME |
| 5 | IFSTWNPWSPYSV |
| 6 | FSWFGSHLLSGGS |
| 7 | FATFFGGSVEKFW |
| 8 | WNYGDVGRWWDWQ |
| 9 | WWGFWNGSAAPVW |
| 10 | SSLLYNWLDNTRQMFLPES |
| 11 | WCVWGLGSGCAGGAAVG |
| 12 | WSPDVLRWPWWASGSSE |
| 13 | FWSADFSAEDASAWWGW |
| 14 | FGSWWWGSGAAS |
| 15 | FSPDFLSSWWQTHAGRF |
| 16 | SFFSPYSAFSSWVESAR |
| 17 | WSSFFPLGFSSWSGSVP |
| 18 | FSFSSLPAWSSFWPTST |
| 19 | FSFLSSAVERIYGA |

TABLE 1-continued

| SEQ ID NO: | Bone tropic peptides Amino acid sequence (single letter code) |
|---|---|
| 20 | TWQSYLDLWGWTPTPSL |
| 21 | WPGSGWWWSEGLQRREV |
| 22 | WPMPWWSEWASLHGGKW |
| 23 | WWPHVSGVYGSLPWGPG |
| 24 | LGTFWSSVWRGVDAGGE |
| 25 | VGWGDWWKSGSVWQGAL |
| 26 | FGHFEWPVLGQWK |
| 27 | FLSASMPYLQAWA |
| 28 | FSYFSSPSTWVQW |
| 29 | SSMFKDFDSLVKSWSGRFS |
| 30 | FDIDWSGMRSWWG |
| 31 | SFDLSAFGSLWDRW |
| 32 | FDRWGFGAGAWWDSVAA |
| 33 | VAVASVGAFWSGLSGWA |
| 34 | FSWSSLSDSFGWGSSFS |
| 35 | SLPALPWGFPSWQQGWL |
| 36 | FFTHFYPPYDVRPHPPA |
| 37 | WDFRSLRDWWPPAPSLS |
| 38 | WLSGWSAGWGSVAAPEG |
| 39 | WSNGAWAKWWGVAEEVG |
| 40 | SIFSTWNPWSPYSVSRGSSGK |
| 41 | SWWGFWNGSAAPVWSRGSSGK |
| 42 | SFGSWWWGSGAASSRGSSGK |
| 43 | SLGTFWSSVWRGVDAGGESRGSSGK |
| 44 | SFDIDWSGMRSWWGSRGSSGK |
| 45 | SWDFRSLRDWWPPAPSLSSRGSSGK |

Another embodiment of the invention includes a composition of the formula I:

$X_1$-J-$X_2$-P.

$X_1$ is a peptide that comprises an amino acid sequence of from about 5 to about 50 amino acids for some embodiments, and from about 10 amino acids to about 25 amino acids for other embodiments, and from about 10 amino acids to about 15 amino acids for other embodiments. The peptides are rich in large aromatic amino acid residues, one or more of Phe, Trp, Tyr. For some embodiments, the peptides include a domain or motif of 3 or more large aromatic amino acid residues within a sequence that includes the first 10 contiguous amino acids from the N-terminal end of the amino acid sequence of the peptide. The peptide embodiments have binding specificity for bone; and lack a collagen sequence cell-binding domain characterized by the sequence Gly-Ile-Ala.

J is absent, or is a linker.

$X_2$ is absent, or for some embodiments is a peptide that comprises an amino acid sequence having from about 3 amino acids to about 50 amino acids for some embodiments, and from about 10 amino acids to about 25 amino acids for other embodiments, and from about 10 amino acids to about 15 amino acids for other embodiments. $X_2$ embodiments have binding specificity for a pharmaceutically active agent.

P is absent, or is a pharmaceutically active agent.

In an embodiment where J is absent and $X_2$ is present, $X_2$ is covalently coupled to $X_1$. In an embodiment where J and $X_2$ are absent, P may either be covalently coupled to $X_1$, or non-covalently coupled to $X_1$. In an embodiment where $X_2$ and P are present, P is non-covalently coupled to $X_2$. In one embodiment, $X_1$ comprises an amino acid sequence selected from SEQ ID NOs:1-45, or a sequence that differs from SEQ ID NOs:1-45 by from 1 to 3 amino acids and retains binding specificity for bone.

Other embodiments of the invention include methods for coating a surface of bone with a peptide and/or composition embodiment, so that one or more of osteoinduction, osteoconduction, and/or osteogenesis is enhanced, compared to bone not treated with the peptide and/or composition. Also included is a method for manufacturing bone incorporating a peptide and/or composition embodiment.

Embodiments described herein include peptides having binding specificity for bone. Embodiments also include a coating composition that includes peptide embodiments. Embodiments also include a coating for bone, method embodiments for coating bone, and bone coated with these compositions.

Embodiments described herein include delivery system embodiments that can do one or more of deliver, localize, recruit, and/or support one or more pharmaceutically active agents to bone, in promoting one or more of osteoinduction, osteoconduction, and/or osteogenesis. Such delivery system embodiments are useful, for example, in diseases or conditions in which a desired outcome is enhancing bone formation.

DEFINITION SECTION

Various terms relating to the biological molecules of embodiments described herein are used throughout the specification and claims. These terms include the following.

The term "bone" as used herein refers to one or more substances comprising autograft bone, allograft bone, xenograft bone, cortical bone, cancellous bone, continuous bone, demineralized bone, discontinuous bone, cut bone pieces, bone chips, particulate bone, bone rings, ground bone, mineralized bone, demineralized bone matrix, bone substitutes containing Type I collagen, bone composites containing Type I collagen, bone implants containing Type I collagen, Type I collagen fibers in a conformation typically associated with bone structure or in a matrix for support of bone growth (the latter, being osteoconductive), and a combination thereof. Bone may be in any suitable form, including for example, as a solid, powder, paste, filler, binder, gel, sponge, implant, graft, a bone cement (e.g., a bone cement impregnated with demineralized bone matrix and/or inorganic bone), and combinations thereof. A preferred type or composition of bone may be used in accordance with the present invention to the exclusion of a type or composition of bone other than the preferred type or composition of bone.

The terms "an embodiment", "embodiment", "embodiments", "the embodiment", "the embodiments", "one or more embodiments", "some embodiments", "one embodiment" and the like mean "one or more (but not all) disclosed embodiments", unless expressly specified otherwise.

The terms "the invention" and "the present invention" and the like mean "one or more embodiments of the present invention."

A reference to "another embodiment" in describing an embodiment does not imply that the referenced embodiment is mutually exclusive with another embodiment (e.g., an embodiment described before the referenced embodiment), unless expressly specified otherwise.

The terms "including", "comprising" and variations thereof mean "including but not limited to", unless expressly specified otherwise.

The terms "a", "an" and "the" mean "one or more", unless expressly specified otherwise.

The term "herein" means "in the present application, including anything which may be incorporated by reference", unless expressly specified otherwise.

The phrase "at least one of", when such phrase modifies a plurality of things (such as an enumerated list of things) means any combination of one or more of those things, unless expressly specified otherwise The term "effective amount" as used herein, refers to an amount of a coating composition embodiment sufficient to (a) mediate binding of the coating composition to the at least one surface of bone in forming a coating; and (b) promote attachment of a pharmaceutically active agent.

The term "individual", as used herein, refers to either a human or an animal.

The term "pharmaceutically active agent", as used herein, refers to one or more agents within a group that includes growth factor, cells, therapeutic drug, hormone, vitamin, and nucleic acid embodiments encoding any of the foregoing. Hormones involved in bone formation include, but are not limited to parathyroid hormone, PTH, including, for example, PTH 1 to PTH 34, and growth hormone. Therapeutic drugs useful in the treatment or prevention of bone diseases or disorders include, but are not limited to, chemotherapeutic agents, such as methotrexate, cyclophosphamide, taxol, adriamycin, or other antineoplastic agent, antimicrobials, such as, antifungal, and/or antibacterial; antibiotics, anti-inflammatory agents, steroidal or nonsteroidal, glucocorticosteroids, and nucleic acid molecules that can affect gene regulation such as DNA, antisense RNA, interfering RNAs, such as RNAi, siRNA, and other RNA molecules or RNA fragments, such as micro-RNA. Vitamins useful in bone formation or prevention of bone diseases or disorders may include but are not limited to, vitamin D, and vitamin D derivatives, such as 1, 25-dihydroxyvitamin D3, 1α-hydroxyvitamin D2, vitamin A, vitamin C, and vitamin K, such as vitamin K2. A preferred pharmaceutically active agent may be used in accordance with the present invention to the exclusion of a pharmaceutically active agent other than the preferred pharmaceutically active agent.

The term "pharmaceutically acceptable carrier", when used herein for purposes of the specification and claims, refers to a carrier medium that is a suitable support medium for administration and/or application of a compound or composition according to the present invention. Pharmaceutically acceptable carriers include peptide or coating composition embodiments to which it is added.

The term "cells", as used herein, refers to one or more cells or cell types useful in invention embodiments described herein, and may include stem cells, chondrocytes, osteoprogenitor stem cells, mesenchymal stem cells, osteocytes, osteoblasts, osteoclasts, periosteal stem cells, bone marrow endothelial cells, stromal cells, adipose tissue precursor cells, and combinations thereof.

The term "growth factor", as used herein, refers to one or more growth factors or cytokines useful in embodiments described, and may include but is not limited to, bone morphogenetic protein, BMP, including the family of BMPs, such as BMP-2, BMP-2A, BMP-2B, BMP-3, BMP-4, BMP-5, BMP-6, BMP-7, BMP-8, BMP-9, BMP-10, BMP-11, BMP-12, BMP-13, BMP-14, BMP-15, BMP-16, BMP-17, and BMP-18, transforming growth factor beta, TGF-beta, transforming growth factor alpha, TGF-alpha, vascular endothelial cell growth factor, VEGF, including its variants, epidermal growth factor, EGF, fibroblast growth factor, such as basic fibroblast growth factor, acidic fibroblast growth factor, FGF-1 to FGF-23, epidermal growth factor, EGF, insulin-like growth factor (I or II), interleukin-I, interferon, tumor necrosis factor, nerve growth factor, neurotrophins, platelet-derived growth factor, PDGF, heparin-binding growth factor, HBGF, hepatocytic growth factor, keratinocyte growth factor, macrophage colony stimulating factor, growth and differentiation factor, such as GDF4 to GDF8, isoforms thereof, biologically active analogs thereof, and a combination thereof. Typically, a biologically analog has an amino acid sequence having from about 1% to about 25% of the amino acids substituted, as compared to the amino acid sequence of the peptide growth factor from which the analog was derived. For peptides less than or equal to 50 amino acids in length, typically a biologically active analog thereof has between 1 and 10 amino acid changes, as compared to the amino acid sequence of the peptide from which the analog was derived.

The term "time sufficient for binding" refers to a temporal duration sufficient for specific binding of a binding domain described herein.

The terms "binds specifically" or "binding specificity", and like terms used herein, are interchangeably used, to refer to the ability of a peptide to have a binding affinity that is greater for one target molecule selected to be bound, "target surface material" over another molecule or surface material other than the target molecule or target surface material. For instance, a binding specificity is an affinity for a given substrate in a heterogeneous population of other substrates which is greater than, for example, that attributable to non-specific adsorption. For example, a peptide has binding specificity for bone when the peptide demonstrates preferential binding to bone including a component of bone, such as Type I collagen, as compared to binding to another biological component not found in bone, or as compared to a material used as a substitute matrix for bone, such as a material that includes beta tricalcium phosphate. This preferential binding is dependent upon the presence of a particular conformation, structure, and/or charge on or within the peptide and/or material for which it has binding specificity.

The term "osteoinductive" refers to the ability of a substance to induce bone growth. More particularly, osteoinduction is the biologically-mediated recruitment and differentiation of cell types essential for bone growth.

The term "osteoconductive" refers to the ability of a substance to support or conduct bone growth.

The term "osteogenesis" refers to the process of bone formation, such as by osteoblastic activity.

The term "peptide" is used herein, refers to an amino acid chain of no less than about 3 amino acids and no more than about 100 amino acid residues in length, wherein the amino acid chain includes naturally occurring amino acids, synthetic amino acids, genetically encoded amino acids, non-genetically encoded amino acids, and combinations thereof; however, specifically excluded from the scope and definition of "peptide" herein is an antibody. For some embodiments, the peptide includes a binding domain having a contiguous sequence of no less than 7 amino acids and no more than about 50 amino acids in length, and multimers of the peptide; that is, linking more than one peptide to a branched polymeric linker using methods known in the art. A peptide for some embodiments, is produced by chemical synthesis, recombinant expression, biochemical or enzymatic fragmentation of a larger molecule, chemical cleavage of larger molecule, a combination of the foregoing or, in general, made by any other methods in the art, and, for some embodiments, isolated. The term "isolated" means that the peptide is substantially free of components which have not become part of the integral structure of the peptide itself. Isolated peptides are substantially free of cellular material or culture medium when produced by recombinant techniques, or substantially free of chemical precursors or other chemicals when chemically synthesized or produced using biochemical or chemical processes. A preferred peptide may be used in accordance with the present invention to the exclusion of a peptide other than the preferred peptide.

The term "linker" as used herein, refers to a compound or moiety that acts as a molecular bridge to couple at least two different molecules such as, coupling at least one peptide having binding specificity for bone to at least one peptide having binding specificity for a pharmaceutically active agent. Thus, for example, one portion of the linker binds to at least one peptide having binding specificity for bone, and another portion of the linker binds to at least one peptide having binding specificity for a pharmaceutically active agent. For some embodiments, two peptides may be coupled to the linker in a step-wise manner, or may be coupled simultaneously to the linker, to form a coating composition embodiment described herein. There is no particular size or content limitations for the linker so long as it can fulfill its purpose as a molecular bridge, and that the binding specificity of each peptide in a coating composition is substantially retained.

The term "coating composition", as used herein, refers to a composition comprising formula I:

$X_1$-J-$X_2$-P, which is described above.

For some embodiments wherein the coating composition includes a peptide having binding specificity for bone, $X_1$, coupled to a peptide having binding specificity for a pharmaceutically active agent, $X_2$, the peptides are coupled together either physically, chemically, synthetically, or biologically, in such a way that each retains its respective function to bind to the respective molecule for which it has binding specificity. This coupling includes forming a multimeric molecule having two or more peptides having binding specificity for bone, two or more peptides having binding specificity for a pharmaceutically active agent, and a combination thereof. For example, using conventional reagents and methods of peptide chemistry, two peptides may be coupled via a side chain-to-side chain bond, in one embodiment, where each of the peptides has a side chain amine, such as the epsilon amine of lysine, a side chain-to-N terminal bond such as coupling the N-terminal amine of one peptide with the side chain amine of the other peptide, a side chain-to-C-terminal bond, such as coupling the C-terminal chemical moiety, carboxyl for some embodiments, of one peptide with the side chain amine of the other peptide, an N-terminal-to-N-terminal bond, an N-terminal to C-terminal bond, a C-terminal to C-terminal bond, or a combination thereof. In synthetic or recombinant expression, a peptide having binding specificity for bone is coupled directly to a peptide having binding specificity for a pharmaceutically active agent by synthesizing or expressing both peptides as a single peptide. The coupling of two or more peptides is via a linker for some embodiments, to form a coating composition.

Coating composition embodiments include the at least one peptide having binding specificity for bone in an amount effective to mediate the binding of the coating composition to a surface of bone to be coated. Thus, the composition provides for targeting and localizing a pharmaceutically active agent to bone. In one embodiment, the coating composition includes at least one peptide having binding specificity for bone and at least one peptide having binding specificity for a pharmaceutically active agent, wherein the at least one peptide having binding specificity for bone and the at least one peptide having binding specificity for a pharmaceutically active agent are coupled together. In another embodiment, the coating composition includes at least one peptide having binding specificity for bone, and at least one peptide having binding specificity for a pharmaceutically active agent, wherein the at least one peptide having binding specificity for bone and the at least one peptide having binding specificity for a pharmaceutically active agent are coupled together, and wherein the at least one peptide having binding specificity for a pharmaceutically active agent is bound to a pharmaceutically active agent for which it has binding specificity. In one embodiment, a linker is used to couple the at least one peptide having binding specificity for bone and the at least one peptide having binding specificity for a pharmaceutically active agent.

The at least one peptide having binding specificity for bone includes, for some embodiments, one or more peptides having binding specificity for bone. For one embodiment the peptide includes one amino acid sequence, such as SEQ ID NO:43, or may include two or more peptides in embodiments linked by a multi-branched linker. In other embodiments, each peptide is a separate component of the composition that includes either (a) the same amino acid sequence, such as SEQ ID NO:39 or (b) two or more amino acid sequences such as, one peptide that includes the amino acid sequence of SEQ ID NO:41, another peptide including the amino acid sequence of SEQ ID NO:42, or other SEQ ID NO. The at least one peptide having binding specificity for a pharmaceutically active agent includes, for some embodiments, a peptide having binding specificity for a single type of pharmaceutically active agent such as a peptide having binding specificity for cells, or includes two or more peptides that include either (a) the same binding specificity such as for DBM; such as peptide comprising an amino acid sequence of SEQ ID NO: 91, and peptide including an amino acid sequence of SEQ ID NO: 118, or other SEQ. ID NO. or (b) two or more amino acid sequences having different binding specificities such as one peptide having a binding specificity for a growth factor, and another peptide having binding specificity for a hormone, or other function.

Linkers used in embodiments described herein include, chemical chains, chemical compounds such as reagents, and the like. The linkers include, but are not limited to, homobifunctional linkers and heterobifunctional linkers. Heterobifunctional linkers contain one end having a first reactive functionality or chemical moiety to specifically link a first molecule, and an opposite end having a second reactive functionality to specifically link to a second molecule. A variety of bifunctional or polyfunctional reagents, both homo- and hetero-functional such as those described in the catalog of the Pierce Chemical Co., Rockford, Ill., amino acid linkers typically, a short peptide of between 3 and 15 amino acids, and often containing amino acids such as glycine, and/or serine, and polymers (e.g., polyethylene glycol) may be employed as a linker with respect to embodiments described herein. In one embodiment, representative peptide linkers include multiple reactive sites to be coupled to a binding domain such as polylysines, polyornithines, polycysteines, polyglutamic acid and polyaspartic acid or include substantially inert peptide linkers such as lipolyglycine, polyserine, polyproline, polyalanine, and other oligopeptides that includes alanyl, serinyl, prolinyl, or glycinyl amino acid residues. In some embodiments wherein an amino acid linker is chosen, the coating composition may be synthesized to a single, contiguous peptide that includes a peptide having binding specificity for bone, a linker, and a peptide having binding specificity for a pharmaceutically active agent. Thus, the linker attachment is via the bonds of the single contiguous peptide.

Suitable polymeric linkers include a synthetic polymer or a natural polymer. Representative synthetic polymers include but are not limited to polyethers such as, poly(ethylene glycol) "PEG", polyesters such as, polylactic acid PLA and polyglycolic acid PGA, polyamines, polyamides such as nylon, polyurethanes, polymethacrylates such as, polymethylmethacrylate; PMMA, polyacrylic acids, polystyrenes, polyhexanoic acid, flexible chelators such as EDTA, EGTA, and other synthetic polymers which have a molecular weight of about 20 daltons to about 1,000 kilodaltons. Representative natural polymers include but are not limited to hyaluronic acid, alginate, chondroitin sulfate, fibrinogen, fibronectin, albumin, collagen, calmodulin, and other natural polymers which, for some embodiments, have a molecular weight of about 200 daltons to about 20,000 kilodaltons for constituent monomers. Polymeric linkers include a diblock polymer, a multi-block copolymer, a comb polymer, a star polymer, a dendritic or branched polymer, a hybrid linear-dendritic polymer, a branched chain comprised of lysine, or a random copolymer. A linker also includes a mercapto(amido)carboxylic acid, an acrylamidocarboxylic acid, an acrlyamidoamidotriethylene glycolic acid, 7-aminobenzoic acid, and derivatives thereof. Linkers also utilize, for some embodiments, copper-catalyzed azide-alkyne cycloaddition such as, "click chemistry" or any other conventional methods. Linkers include linkers that can be cleaved, and linkers that can be made reactive toward other molecular moieties or toward themselves, for cross-linking purposes.

Depending upon such factors as the molecules to be linked, and the conditions in which the linking is performed, the linker varies in length and composition for optimizing such properties as preservation of biological function, stability, resistance to certain chemical and/or temperature parameters, and of sufficient stereo-selectivity or size. For example, the linker should not significantly interfere with the ability of a coating composition to sufficiently bind, with appropriate affinity for the purpose, to a bone for which it has specificity according to embodiments described herein, or the ability of a coating composition to sufficiently bind, with appropriate affinity for the purpose, to a pharmaceutically active agent for which it has specificity. Linkers include one or more molecules having activities which enhance or complement the effect of the coating composition embodiments described herein.

In some embodiments, a peptide that binds specifically to a particular surface, material or composition binds at least 10%, 20%, 30%, 40%, 50%, 60%, 70%, 80%, 90%, 100%, 200%, 300%, 400%, 500%, or a higher percentage, than the peptide binds to an appropriate control such as, for example, a different material or surface, or a protein typically used for such comparisons such as bovine serum albumin. Binding specificity can be determined by an assay in which quantitated is a signal, such as fluorescence, or colorimetric representing the relative amount of binding between a peptide and bone, as compared to peptide and materials other than bone or other than Type I collagen matrices. In one embodiment, a peptide has a binding specificity that is characterized by a relative binding affinity as measured by an EC50 of 10 μM or less, and for some embodiments, less than 1 μM. The EC50 is determined using any number of methods known in the art, such as by generating a concentration response curve from a binding assay in which the concentration of the peptide is titered with a known amount of the substrate for which the peptide has binding specificity. In this case, the EC50 represents the concentration of peptide producing 50% of the maximal binding observed for that peptide in the assay.

Peptides usable in embodiments described herein include L-form amino acids, D-form amino acids, or a combination thereof. Representative non-genetically encoded amino acids include but are not limited to 2-aminoadipic acid; 3-aminoadipic acid; β-aminopropionic acid; 2-aminobutyric acid; 4-aminobutyric acid (piperidinic acid); 6-aminocaproic acid; 2-aminoheptanoic acid; 2-aminoisobutyric acid; 3-aminoisobutyric acid; 2-aminopimelic acid; 2,4-diaminobutyric acid; desmosine; 2,2'-diaminopimelic acid; 2,3-diaminopropionic acid; N-ethylglycine; N-ethylasparagine; hydroxylysine; allo-hydroxylysine; 3-hydroxyproline; 4-hydroxyproline; isodesmosine; allo-isoleucine; N-methylglycine (sarcosine); N-methylisoleucine; N-methylvaline; norvaline; norleucine; ornithine; and 3-(3,4-dihydroxyphenyl)-L-alanine ("DOPA"). Representative derivatized amino acids include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups can be derivatized to form salts, methyl and ethyl esters or other types of esters or hydrazides. Free hydroxyl groups can be derivatized to form O-acyl or O-alkyl derivatives. The imidazole nitrogen of histidine can be derivatized to form N-im-benzylhistidine. In one embodiment, a coating composition, includes at least one peptide having binding specificity for bone and has an N-terminal amino acid, a C-terminal amino acid, or a combination thereof, wherein such amino acid is a non-genetically encoded amino acid that enhances the binding avidity, a strength of binding interactions, of the peptide to bone. Such amino acids can be incorporated into a peptide by conventional methods for solid phase and/or solution phase synthesis. For example, in one embodiment, from about one to about three residues of DOPA, a hydroxy-amino acid such as one or more of hydroxylysine, allo-hydroxylysine, hydroxyproline, or a combination thereof, is added as terminal amino acids of an amino acid sequence of a peptide during synthesis, wherein the peptide is used in the coating composition embodiments described herein for enhancing the strength of the binding interactions via electrostatic or ionic interactions between the coating composition and the at least one bone surface to be coated.

Peptide embodiments described herein include modification, such as by addition of chemical moieties, or substitutions, insertions, and deletions of amino acids, where such modifications provide for certain advantages in its use. Thus, peptides usable herein include any of a variety of forms of peptide derivatives including, for example, amides, conjugates with proteins, cyclone peptides, polymerized peptides, conservatively substituted variants, analogs, fragments, chemically modified peptides, and peptide mimetics. Any peptide derivative that has desired binding characteristics of the family of peptides according to embodiments described herein can be used. For example, a chemical group, added to the N-terminal amino acid of a synthetic peptide to block chemical reactivity of that amino terminus of the peptide, includes an N-terminal group. Such N-terminal groups for protecting the amino terminus of a peptide include, but are not limited to, lower alkanoyl groups, acyl groups, sulfonyl groups, and carbamate forming groups. Usable N-terminal groups may include acetyl, Fmoc, and Boc. A chemical group, added to the C-terminal amino acid of a synthetic peptide to block chemical reactivity of that carboxy terminus of the peptide, includes a C-terminal group. Such C-terminal groups for protecting the carboxy terminus of a peptide include, an ester or amide group. Terminal modifications of a peptide are often useful to reduce susceptibility to proteinase digestion, and to therefore prolong the half-life of peptides in the presence of biological fluids where proteases can be present. Optionally, a peptide, as described herein, comprise one or more amino acids that have been modified to contain one or more chemical groups such as reactive functionalities such as fluorine, bromine, or iodine to facilitate linking the peptide to a linker molecule. Usable peptides also include peptides where one or more of the peptide bonds are replaced by pseudopeptide bonds including but not limited to a carba bond ($CH_2$—$CH_2$), a depsi bond (CO—O), a hydroxyethylene bond (CHOH—$CH_2$), a ketomethylene bond (CO—$CH_2$), a methylene-oxy bond ($CH_2$—O), a reduced bond ($CH_2$—NH), a thiomethylene bond ($CH_2$—S), an N-modified bond (—NRCO—), and a thiopeptide bond (CS—NH).

Peptides usable in a coating composition or method of using the coating composition according to embodiments described herein, also include peptides having one or more substitutions, additions and/or deletions of residues relative to the sequence of an exemplary peptide embodiments disclosed in Table 1 and SEQ ID NOs:1-45 herein, so long as the binding properties of the original exemplary peptide are substantially retained. Thus, embodiments include peptides that differ from the exemplary sequences disclosed herein by about 1, 2, 3, 4, 5, 6, 7, 8, 9, or 10 amino acids depending on the length of the exemplary peptide disclosed herein, and that share sequence identity with the exemplary sequences disclosed herein of at least 70%, 75%, 80%, 81%, 82%, 83%, 84%, 85%, 86%, 87%, 88%, 89%, 90%, 91%, 92%, 93%, 94%, 95%, 96%, 97%, 98%, 99%, or greater sequence identity. Sequence identity may be calculated manually or it may be calculated using a computer implementation of a mathematical algorithm, for example, GAP, BESTFIT, BLAST, FASTA, and TFASTA, or other programs or methods known in the art. Alignments using these programs can be performed using the default parameters.

A peptide having an amino acid sequence substantially identical to a sequence of an exemplary peptide disclosed herein may have one or more different amino acid residues as a result of substituting an amino acid residue in the sequence of the exemplary peptide with a functionally similar amino acid residue, a "conservative substitution"; provided that peptide containing a conservative substitution substantially retains the binding specificity of the exemplary peptide not containing the conservative substitution. Examples of conservative substitutions include the substitution of one non-polar (hydrophobic) residue such as isoleucine, valine, leucine or methionine for another; the substitution of one aromatic residue such as tryptophan, tyrosine, or phenylalanine for another; the substitution of one polar (hydrophilic) residue for another such as between arginine and lysine, between glutamine and asparagine, between threonine and serine; the substitution of one basic residue such as lysine, arginine or histidine for another; or the substitution of one acidic residue such as aspartic acid or glutamic acid for another.

In yet another embodiment, a binding domain includes a peptide having at least 70% identity thereto, and for some embodiments at least 95% identity thereto, along with additional amino acids at the carboxyl and/or amino terminal ends, ranging from about 1 to about 20 additional amino acids at one end or at each of both ends which maintains the primary activity of the peptides as a binding domain described herein. Thus, as a non-limiting example, a peptide of any one of the amino acid sequences illustrated as SEQ ID NOs: 1-45 possess the activity of binding bone with binding specificity, as provided herein; and does not possess any characteristics which constitutes a material change to the basic and novel characteristics of the peptide to function as a binding domain by binding bone.

Examples of pharmaceutical acceptable carriers include aqueous solutions, aqueous or non-aqueous solvents, suspensions, emulsions, gels, pastes, and the like. Suitable pharmaceutically acceptable carrier include one or more substances, including but not limited to, water, buffered water, medical parenteral vehicles, saline, 0.3% glycine, aqueous alcohols, isotonic aqueous buffer; and may further include one or more substances such as water-soluble polymer, glycerol, polyethylene glycol, glycerin, oils, salts such as sodium, potassium, magnesium and ammonium, phosphonates, carbonate esters, fatty acids, saccharides, polysaccharides, glycoproteins (for enhanced stability), excipients, and preservatives and/or stabilizers to increase shelf-life or as necessary and suitable for manufacture and distribution of the composition.

Embodiments of the invention include peptides having binding specificity for bone, coating compositions that include peptide embodiments having specificity for bone, method embodiments for coating bone with a coating composition, and bone coated with a coating composition that includes at least one peptide having binding specificity for bone. In one embodiment, the coating composition includes one or more peptides having binding specificity for bone, and for some embodiments, further includes a pharmaceutically acceptable carrier. Exemplary peptides include a peptide comprising an amino acid selected from the group consisting of SEQ ID NOs: 1 to 45. In another embodiment, the coating composition includes at least one peptide having binding specificity for bone, the peptide being coupled to at least one peptide having binding specificity for a pharmaceutically active agent. In another embodiment, the coating composition includes at least one peptide having binding specificity for bone, the at least one peptide being coupled to at least one peptide having binding specificity for a pharmaceutically active agent having pharmaceutically active agent bound thereto. Some coating composition embodiments further include a pharmaceutically acceptable carrier. The coating composition is applied to bone in an amount effective to promote the ability of the coated bone to be one or more of osteoinductive, osteoconductive, and osteogenic, as compared to bone not coated with a coating composition embodiment. Embodiments of the invention are illustrated in the following examples, which are not intended to be limiting.

Example 1

Illustrated in this example are various method embodiments for utilizing phage display technology to produce peptides having binding domain embodiments of the invention. In particular, the peptides include binding specificity for bone and binding specificity for a pharmaceutically active agent, respectively.

Phage display technology is usable to identify additional peptides for use as binding domains in the composition embodiments described herein. In general, using phage display, a library of diverse peptides is presented to a target substrate. Peptides that specifically bind to the substrate can be selected for use as binding domains. Multiple serial rounds of selection, called "panning," may be used. Any one of a variety of libraries and panning methods can be employed to identify a binding domain that is useful in a coating composition embodiment described herein. Panning methods include, for example, solution phase screening, solid phase screening, or cell-based screening. Once a candidate binding domain is identified, directed or random mutagenesis of the sequence are used to optimize the binding properties including one or more of specificity and avidity of the binding domain.

A. A variety of different phage display libraries were screened for peptides that bind to a selected target substrate. In particular, a substrate selected to find a binding domain useful in embodiments of the present invention were screened. The substrate was either bound to or placed in, depending on the selected substrate a container such as wells of a 96 well microtiter plate, or a microfuge tube. Nonspecific binding sites on the surfaces of the container were blocked with a buffer containing bovine serum albumin ("BSA") in a range of from 1% to 10%. The containers were then washed 5 times with a buffer containing buffered saline with Tween™ 20, "buffer-T". Each library was diluted in buffer-T and added at a concentration of $10^{10}$ pfu/ml in a total volume of 100 µl. After incubation for 1 to 3 hours at room temperature with shaking at 50 rpm, unbound phage were removed by multiple washes with buffer-T. Bound phage were used to infect *E. coli* cells in growth media. The cell and phage-containing media was cultured by incubation overnight at 37° C. in a shaker at 200 rpm. Phage-containing supernatant was harvested from the culture after centrifuging the culture. Second and third rounds of selection were performed in a similar manner to that of the first round of selection, using the amplified phage from the previous round as input. To detect phage that specifically bind to the selected substrate, enzyme-linked immunosorbent (ELISA-type) assays were performed using an anti-phage antibody conjugated to a detector molecule, followed by the detection and quantitation of the amount of detector molecule bound in the assay. The DNA sequences encoding peptides from the phage that specifically bind to the selected substrate were then determined. For example, the sequence encoding the peptide is located as an insert in the phage genome, and can be sequenced to yield the corresponding amino acid sequence displayed on the phage surface.

As a specific illustrative example, demineralized bone matrix, "DBM", was used as a bone substrate for performing phage selection using several different libraries of phage. To 50 mg of DBM was added 1 ml buffer-T, followed by mixing for 1 hour. The mixture was then centrifuged, and the buffer was aspirated from the centrifuge tube. To each tube was added 900 µl of Tris-buffered saline containing 10% bovine serum albumin, and the tubes were mixed to resuspend the DBM. The tubes were then incubated for 30 minutes with rotation at room temperature. To each tube was added 100 µl of a phage library to be selected, and the tubes were then incubated for 1 hour at room temperature with rotation. The tubes were then centrifuged to pellet the DBM, and the supernatant was aspirated. The DBM containing bound phage was then washed 4 times with buffer-T. The DBM containing bound phage were then mixed with 1 ml of log-phase *E. coli* in growth media, and incubated at 37° C. for 30 minutes. The DBM was then allowed to settle in the tube, and then the medium containing the phage-infected cells was removed and placed into a new tube. Serial dilutions of the infected cells were performed to determine phage titer for input into the next round of selection. Second, third and fourth rounds of selection were performed in a similar manner to that of the first round, using supernatant containing amplified phage from the previous round as input for the next round, and 20 mg DBM.

Individual phage were analyzed for their binding specificity in an ELISA format. Blocking of microtiter wells and DBM contained therein was accomplished using a 1 hour incubation with buffer containing 1% BSA. To each microtiter well was added phage-containing supernatant, and buffer containing 1% BSA. After a 1 hour binding reaction, the DBM in each well was washed three times with buffer-T. To detect phage that specifically bound to DBM, a conventional ELISA was performed using an anti-M13 phage antibody conjugated to horseradish-peroxidase, followed by the addition of chromogenic agent 3,3,5,5' tetramethylbenzidine, and determining a read-out at 650 nm. Relative binding strengths of the phage can also be determined by testing serial dilutions of the phage for binding to DBM in an ELISA. The DNA sequence encoding peptides that specifically bound DBM was determined. The sequence encoding the peptide insert was located in the phage genome and translated to yield the corresponding amino acid sequence displayed on the phage surface.

B. Binding Domain Characterizations and Synthesis:

Relative binding strengths of the peptides to bone, also used as a measure of binding specificity, were determined by testing serial dilutions of the peptide for binding to bone, as represented by DBM. Plotting the absorbance observed across the concentration range for each peptide sequence yielded a binding curve of the peptides to its target substrate from which can be determined an EC50. The goal of the screenings and selections was to identify one or more peptides that bind to the selected substrate with binding specificity, with an EC50 of less than or equal to about 10 µM, and for some embodiments, in the nanomolar range (<1 µM). Thus, in one embodiment, a binding domain includes a peptide demonstrating binding specificity for the selected target (e.g., DBM) with an EC50 of less than or equal to about 10 µM, and more preferably, in the nanomolar range (<1 µM).

As a specific example, DBM was placed in a microtiter plate at a concentration of 3 mg equivalents per well, and then the wells were blocked with buffer containing 1% BSA for 1 hour at room temperature. The buffer containing 1% BSA was then aspirated from each well, and added to the wells were the serial dilutions of biotinylated peptide. The microtiter plates were incubated for 1 hour at room temperature on a plate shaker. The DBM was then allowed to settle, and the buffer was then aspirated from the wells. The DBM was washed three times with buffer-T, and then streptavidin-alkaline phosphatase was added. The microtiter plates were incubated for 1 hour at room temperature on a plate shaker. The DBM was then allowed to settle, and the buffer was then aspirated from the wells. The DBM was washed three times with buffer-T, pNPP (p-nitrophenyl phosphate) was used to develop the assay, and the absorbance was recorded at 405 nm. An estimate of the relative affinity (binding specificity, EC50) of a peptide for bone can be made by determining the concentration of peptide that gives one-half the maximal signal in the assay.

Peptides may be synthesized by any method for peptide synthesis including, but not limited to, solid phase synthesis, solution phase synthesis, and a combination thereof. For example, peptides that include binding domains useful in embodiments described herein were synthesized on a peptide synthesizer using standard solid-phase synthesis techniques, and using standard FMOC peptide chemistry. After all residues were coupled, simultaneous cleavage and side chain deprotection was performed using conventional methods and reagents. After cleavage from the resin, the peptides were precipitated, and the precipitate was lyophilized. The peptides were then purified using reverse-phase high performance liquid chromatography; and peptide identity was confirmed with mass spectrometry.

Example 2

Using the methodology described in Example 1 herein, exemplary peptides having binding specificity for bone have been developed. A list of peptide embodiments is shown in Table 2. While typically such phage amino acids adjoining the peptide displayed had no significant contribution to the binding specificity of the peptide, the peptide embodiments described herein may include, in their amino acid sequence, such phage amino acids adjoining the peptide at the N-terminus and at the C-terminus (e.g., S and SR, respectively; see, for example, Table 3).

TABLE 2

| SEQ ID NO: | Bone tropic peptides Amino acid sequence (single letter code) |
|---|---|
| 1 | FYSIFFPQMGGSM |
| 2 | FSGWFLPWEGRSE |
| 3 | FYWPSFNSGNSLW |
| 4 | FSWFSYPSQLWME |
| 5 | IFSTWNPWSPYSV |
| 6 | FSWFGSHLLSGGS |
| 7 | FATFFGGSVEKFW |
| 8 | WNYGDVGRWWDWQ |
| 9 | WWGFWNGSAAPVW |
| 10 | SSLLYNWLDNTRQMFLPES |
| 11 | WCVWGLGSGCAGGAAVG |
| 12 | WSPDVLRWPWWASGSSE |
| 13 | FWSADFSAEDASAWWGW |
| 14 | FGSWWWGSGAAS |
| 15 | FSPDFLSSWWQTHAGRF |
| 16 | SFFSPYSAFSSWVESAR |
| 17 | WSSFFPLGFSSWSGSVP |
| 18 | FSFSSLPAWSSFWPTST |
| 19 | FSFLSSAVERIYGA |
| 20 | TWQSYLDLWGWTPTPSL |
| 21 | WPGSGWWWSEGLQRREV |
| 22 | WPMPWWSEWASLHGGKW |
| 23 | WWPHVSGVYGSLPWGPG |
| 24 | LGTFWSSVWRGVDAGGE |

TABLE 2-continued

| SEQ ID NO: | Bone tropic peptides Amino acid sequence (single letter code) |
|---|---|
| 25 | VGWGDWWKSGSVWQGAL |
| 26 | FGHFEWPVLGQWK |
| 27 | FLSASMPYLQAWA |
| 28 | FSYFSSPSTWVQW |
| 29 | SSMFKDFDSLVKSWSGRFS |
| 30 | FDIDWSGMRSWWG |
| 31 | SFDLSAFGSLWDRW |
| 32 | FDRWGFGAGAWWDSVAA |
| 33 | VAVASVGAFWSGLSGWA |
| 34 | FSWSSLSDSFGWGSSFS |
| 35 | SLPALPWGFPSWQQGWL |
| 36 | FFTHFYPPYDVRPHPPA |
| 37 | WDFRSLRDWWPPAPSLS |
| 38 | WLSGWSAGWGSVAAPEG |
| 39 | WSNGAWAKWWGVAEEVG |

Example 1 illustrates methods to determine the relative binding strengths of peptide to bone. As shown in Table 3, six peptides including the amino acid sequences illustrated as SEQ ID NOs: 5, 9, 14, 24, 30, and 37 were synthesized to include an amino linker containing glycine, serine, and lysine to facilitate biotinylation of these peptides for determining the relative binding strengths to bone. A biotin molecule was linked to the C-terminal lysine. Also shown in Table 3 are the relative binding strengths expressed as EC50 (μM) to bone as represented by DBM of human origin. It is noted that the EC50 values were the same or substantially similar when DBM of rabbit origin was used.

TABLE 3

| SEQ ID NO: | Binding specificity for bone (e.g., DBM) Amino acid sequence (single letter code) | EC50 (μM) |
|---|---|---|
| 40 | SIFSTWNPWSPYSVSRGSSGK | <1 |
| 41 | SWWGFWNGSAAPVWSRGSSGK | <0.1 |
| 42 | SFGSWWWGSGAASSRGSSGK | <0.1 |
| 43 | SLGTFWSSVWRGVDAGGESRGSSGK | <1 |
| 44 | SFDIDWSGMRSWWGSRGSSGK | <1 |
| 45 | SWDFRSLRDWWPPAPSLSSRGSSGK | <1 |

As illustrated in Tables 2 and 3, peptide embodiments include:
(a) a binding specificity for bone as characterized by an EC50 of less than or equal to about 10 μM, and for some embodiments, in the nanomolar range (<1 μM); (b) from about 10 amino acids to about 25 amino acids, and for some embodiments, from about 10 amino acids to about 15 amino acids; (c) an amino acid sequence rich in large aromatic amino acid residues (one or more of Phe, Trp, Tyr), and for some embodiments include a domain or motif comprised of 3 or more large aromatic amino acid residues within a sequence including the first 10 contiguous amino acids from the N-terminal end of the peptide; and (d) lacks a collagen sequence cell-binding domain characterized by the sequence Gly-Ile-Ala.

Using the methodology illustrated in Example 1, the peptides illustrated in Table 3 were also tested for relative binding strength to demineralized cortical bone, and to cancellous bone, additional evidence of binding specificity for bone. From comparing the different assays and as illustrated in Table 4, the EC50 values obtained when using demineralized cortical bone ("DCB") or using cancellous bone ("CNB") were similar to the EC50 values obtained when using demineralized bone matrix ("DBM"), each as representing bone.

TABLE 4

Bone tropic peptides and binding specificity for various forms of bone

| SEQ ID NO: | EC50 (μM) for DBM | EC50 (μM) for DCB | EC50 (μM) for CNB |
|---|---|---|---|
| 40 | <1 | <1 | <1 |
| 41 | <0.1 | <0.1 | ≦0.1 |
| 42 | <0.1 | <0.1 | <0.5 |
| 43 | <1 | <1 | ≦1 |
| 44 | <1 | <1 | <1 |
| 45 | <1 | <1 | <1 |

While these exemplary peptide sequences are disclosed herein, one skilled in the art will appreciate that the binding properties conferred by those sequences may be attributable to only some of the amino acids that include the sequences. In that regard, binding evidence suggests that a concentration of large aromatic amino acid residues (one or more of Phe, Trp, Tyr), and for some embodiments, a domain or motif comprised of 3 or more large aromatic amino acid residues within a sequence that includes the first 10 amino acids (counting from the N-terminus) contributes significantly to the binding specificity of the peptide to bone. For some embodiments the first 8 amino acids, and for some embodiments the first 5 contiguous amino acids from the N-terminal end of the peptide contribute significantly to the binding specificity of the peptide to bone. For some embodiments including 6 contiguous amino acids, in the N-terminal half, for example, within the first 50% from the N-terminus towards the C-terminus of the amino acid sequence of the peptide including 10 to 20 amino acids, contribute significantly to the binding specificity of the peptide to bone as illustrated below. For example, consider peptide embodiments including amino acid sequences identified in Table 3 as SEQ ID NOs: 41 and 42. Those peptides may be characterized by the following motifs, respectively:

[_ _ _] ←N-terminal half

| ←N-terminal end of peptide

SEQ ID NO: 46 ZZXZZXXXXXXZ;

SEQ ID NO: 47 ZXXZZZXXXXX;

wherein Z is F, phenylalanine, W, tryptophan, or Y, tyrosine; and X is any amino acid.

Exemplary peptide embodiments showed binding specificity when tested in a binding assay for binding specificity to a collagen scaffold (such as a cross-linked matrix of Type I collagen) which has been commonly used as an osteoconductive device. These results and other data signify that peptide embodiments that include a domain or motif that includes 3 or more large aromatic amino acid residues within a sequence including between 5 and 8 contiguous amino acids in the N-terminal half of the amino acid sequence of the peptide appear to preferentially bind Type I collagen in the context of bone itself or a scaffold having osteoconductive properties.

Example 3

This example illustrates peptides comprising a binding domain having a binding specificity for a pharmaceutically active agent, which can be coupled to a peptide having binding specificity for bone, in forming a coating composition.

In one embodiment, the pharmaceutically active agent is a growth factor. One growth factor is selected from one or more Bone Morphogenetic Proteins (BMPs), a distinct subset of the transforming growth factor-beta family best known for their role in bone growth. BMPs induce a cascade of events that leads to new bone formation including the migration of mesenchymal stem cells, the deposition of osteoconductive matrix, the proliferation of osteoprogenitor cells, and the differentiation of progenitor cells into bone-producing cells. Much research has been directed to the use of a BMP on or near bone implants in order to promote one or more of osteoinduction, osteoconduction, and osteogenesis of the implants; however, one of the critical issues that remains unresolved is how to localize BMP on or at the site of the implant. Thus, one coating composition embodiment includes at least one peptide having binding specificity to bone coupled to at least one peptide having binding specificity for BMP. Such coating composition may further include BMP bound to the at least one peptide having binding specificity for BMP.

The BMP-binding peptides fall within 2 families of peptides, distinguished by their respective binding motif ("Motif 1" and "Motif 2"), with Tables 5 & 6 illustrating some exemplary peptides that may be used as binding domains including peptides having binding specificity for BMP in a coating composition. In some embodiments, an exemplary binding domain including a peptide having binding specificity for BMP that includes only that portion of the sequence shown in uppercase letters i.e., the "ss" and "sr" are amino acids of phage sequence origin that adjoin displayed peptide.

Motif 1 for a peptide with binding specificity for BMP (SEQ ID NO:48): Z-X-X-Phe-X-B-Leu; wherein Z=Trp, Phe, or Tyr; X=any amino acid; "B"=Ser, Thr, Ala, or Gly. Note that SEQ ID NO: 91 comprises a consensus sequence.

TABLE 5

| Sequence | SEQ ID NO. |
|---|---|
| ssDWGVVASAWDAFEALDAsr | 49 |
| ssGADFGYGSWVSFSALSAsr | 50 |
| srGEASGWEAFSALEAAVVsr | 51 |
| srSSDSAFSSFSALEGSVVsr | 52 |
| srDGAGAAAWGAFSALASEsr | 53 |
| srGGEAAAGAWVSFSALESsr | 54 |
| srVSGVAAWEAFAGLSVSSsr | 55 |
| srDGGSFSAFSSLVWAADSsr | 56 |

TABLE 5-continued

| Sequence | SEQ ID NO. |
|---|---|
| ssVAGDVGSSWAAFASLAAsr | 57 |
| ssWEVFSSLESGSVGAGAGsr | 58 |
| ssSSGAVSSFESLSGSVVSsr | 59 |
| srEGVAWEAFGALSSFAADsr | 60 |
| ssWGLASEASFFSFSALSSsr | 61 |
| srEGAAWDSFFALSGGSAAsr | 62 |
| ssAPLTESEAWRGFSKLEVsr | 63 |
| ssSMPVGWDSWRGLEWSDRsr | 64 |
| ssEGRGGWNSWEAFRELVVsr | 65 |
| ssGGGGAWESWRGLSGVELsr | 66 |
| srNVEGSWESFAGLSHVREsr | 67 |
| srEDGGRWESFLGLSAVEVsr | 68 |
| ssVEGSAWSAFKSLSSEGVsr | 69 |
| srVEGGAWQALAGLTVERVsr | 70 |
| ssPPKHAWGSFDALGGQVVsr | 71 |
| ssERGVGWEVFLAMEGARMsr | 72 |
| ssSSSGTWQAFTGLSGERVsr | 73 |
| ssSPGGGSGGWDAFYSLVGsr | 74 |
| ssGGGGGGEGFSSLSGNGRsr | 75 |
| ssTGGGSWEEFKAMTPSWTsr | 76 |
| ssEGSGLWDSFSSLSVHEVsr | 77 |
| ssGVTQESASWSSFRTLAVsr | 78 |
| ssSKVAPSGEWRSFATLEVsr | 79 |
| ssEAGRGWEGFKALEGYQVsr | 80 |
| ssLGQTGWEAFESLSGTRGsr | 81 |
| ssVAWDAFTVFESLEGVATsr | 82 |
| ssEVVEPWEWWVALERAGGsr | 83 |
| srVAAVSWEFFGSLSSAGVsr | 84 |
| ssADLGVSGSWEGFALMRGsr | 85 |
| ssVGQMGWEAFESLSGTGGsr | 86 |
| ssGQGETWEWFAGMRGSVAsr | 87 |
| ssYFDVFSSMTGTRAAGSWsr | 88 |
| ssAYSVFSSLRADNSGGAVsr | 89 |
| ssGGIASLKYDVVKTWEsr | 90 |
| GGGAWEAFSSLSGSRV | 91 |

Motif 2 for a peptide with binding specificity for BMP (SEQ ID NO:92):

(Leu or Val)-X-Phe-Pro-Leu-(Lys or Arg)-Gly. Note that SEQ ID NO: 118 comprises a consensus sequence.

TABLE 6

| Sequence | SEQ ID NO. |
| --- | --- |
| ssSVDLYFPLKGDVVsr | 93 |
| ssFEPLRFPLKGVPVsr | 94 |
| ssEGVGGFPLKGIPQEAWAsr | 95 |
| ssPSGVVFPLRGELLGVXKsr | 96 |
| ssGGFVPFPLRGEVWDGVHsr | 97 |
| ssEGSLSFPLKGQVYSGWGsr | 98 |
| ssGKPLEFPLRGTLAEWPVsr | 99 |
| srGEALGFPLTGQLMEAAEsr | 100 |
| ssMWDVGFPLKGRWIDGADsr | 101 |
| ssSNSLWFPLRGSTVEVGAsr | 102 |
| ssGPALRLPLRGTVVSDVPsr | 103 |
| ssADRVAWPLKGAPVWVKEsr | 104 |
| ssGLALGLPIKGWTVSGKDsr | 105 |
| ssGYTLGFPLSGQTIKDWPsr | 106 |
| ssEGWVHFPLKGDVMGGPFsr | 107 |
| ssGRYVSLPLKGEVVPQTAsr | 108 |
| ssEGGVGFPLKGIPQEAWAsr | 109 |
| srVDSVNFPLRGETVTSMVsr | 110 |
| ssEGVGGFPLKGIPQEAWAsr | 111 |
| ssPSGVVFPLRGELLGVXKsr | 112 |
| ssGGFVPFPLRGEVWDGVHsr | 113 |
| ssEGSLSFPLKGQVYSGWGsr | 114 |
| ssGKPLEFPLRGTLAEWPVsr | 115 |
| srGEALGFPLTGQLMEAAEsr | 116 |
| ssMWDVGFPLKGRWIDGADsr | 117 |
| GGALGFPLKGEVVEGWA | 118 |

Exemplary peptides were tested for their ability to bind with specificity to members of the BMP family in an ELISA-format assay. For example, a peptide including an amino acid sequence such as the sequence shown as SEQ ID NO:91 displayed binding specificity for BMP2, BMP4, BMP5, BMP7, and BMP14; whereas a peptide including an amino acid sequence such as any one of SEQ ID NOs: 58, 93, and 118, showed binding specificity for BMP2, BMP4, BMP7, and BMP14. Further, when immobilized to a surface, these peptides demonstrated the ability to extract BMP2 from fluids (each of plasma and bone marrow aspirate) spiked with BMP2. The presence of peptide does not inhibit BMP2 activity. For example, BMP2-mediates transdifferentiation of C2C12 myoblasts into osteoblasts; and when treated with BMP-2, the alkaline phosphatase activity in C2C12 myoblasts was induced.

In another embodiment, the pharmaceutically active agent comprises a cell. Thus, a coating composition embodiment includes at least one peptide having binding specificity to bone coupled to at least one peptide having binding specificity for cells. Such coating composition may further include cells bound to the at least one peptide having binding specificity for the cells. For example, RGDX peptides wherein X is any amino acid (SEQ ID NO:119) have been described as binding stem cells, mesenchymal stem cells, and osteoblasts. A peptide having a sequence of ALPSTSSQMPQL (SEQ ID NO:120) has been described as binding to stem cells. In a further example, a peptide including the amino acid sequence of SSSCQHVSLLRPSAALGPDNCSR (SEQ ID NO:121) has binding specificity for human adipose-derived stem cells, such cells having osteogenic capacity and utility in bone repair or replacement.

In another embodiment, the pharmaceutically active agent comprises a vitamin. Thus, a coating composition embodiment includes at least one peptide having binding specificity to bone coupled to at least one peptide having binding specificity for a vitamin, and for some embodiments, vitamin D. Such coating composition may further include the vitamin bound to the at least one peptide having binding specificity for the vitamin. For example, a peptide derived from the human Vitamin D binding protein, and having the amino acid sequence of LERGRDYEKNKVCKEFSHLGKDDFEDF (SEQ ID NO: 122), has been found to bind to vitamin D sterols.

In another embodiment, the pharmaceutically active agent comprises a therapeutic drug. Thus, a coating composition embodiment includes at least one peptide having binding specificity to bone coupled to at least one peptide having binding specificity for a therapeutic drug. Such coating composition may further include the therapeutic drug bound to the at least one peptide having binding specificity for the therapeutic drug. For example, as a result of using phage display to screen for peptides that bind to paclitaxel, trade name, Taxol®, was a peptide having the amino acid sequence of HTPHPDASIQGV (SEQ ID NO: 123). In another embodiment where the pharmaceutically active agent includes a therapeutic drug, the therapeutic drug comprises an antimicrobial. Thus, a coating composition embodiment includes at least one peptide having binding specificity to bone coupled to at least one peptide having binding specificity for a therapeutic drug comprising an antimicrobial. Such coating composition may further include the therapeutic drug bound to the at least one peptide having binding specificity for the therapeutic drug. For example, vancomycin and vancomycin analogs have been found to bind to bacterial cell wall peptides ending with D-Ala-D-Ala, two D-alanine residues. A peptide that mimics bacterial cell wall peptide binding to vancomycin includes an amino acid sequence of Lys-Ala-Ala (L-Lys-D-Ala-D-Ala).

In another embodiment, the pharmaceutically active agent comprises a hormone. Thus, a coating composition embodiment includes at least one peptide having binding specificity to bone coupled to at least one peptide having binding specificity for a hormone. Such coating composition may further include the hormone bound to the at least one peptide having binding specificity for the hormone. For example, peptides having a core amino acid sequence of VMNV (SEQ ID NO: 124) have been found to bind to human growth hormone.

In another embodiment, the pharmaceutically active agent comprises a nucleic acid molecule, and for some embodiments, a nucleic acid molecule encoding a growth factor, therapeutic drug, hormone, or vitamin. Thus, a coating composition embodiment includes at least one peptide embodiment having binding specificity to bone coupled to at least one peptide having binding specificity for a nucleic acid molecule. Such coating composition further include the nucleic acid molecule bound to the at least one peptide having binding specificity for the nucleic acid molecule. For example, peptide having the amino acid sequence of AEDG (SEQ ID NO: 125) complexes with duplex DNA comprising [poly (dA-dT): poly(dA-dT)].

Using these methods described herein, for example, a binding domain comprising a peptide having binding specificity for bone linked for some embodiments, to a binding domain that includes a peptide having binding specificity for a selected pharmaceutically active agent, in forming a coating composition embodiment. A method of preference for linking a linker molecule to a binding domain will vary according to the reactive groups present on each molecule. As previously described herein, using conventional methods, two binding domains may be coupled by a linker to form a coating composition embodiment by synthesizing a single contiguous peptide that includes a first binding domain, a linker comprising 3 or more amino acids such as including one or more of glycine and serine, and a second binding domain. The terms "first" and "second" are only used for purposes of ease of description, and are not intended to be construed as to limiting the order of the synthesis. In other words, the first binding domain may comprise a peptide having binding specificity for a selected pharmaceutically active agent, and the second binding domain may include a peptide having binding specificity for bone; or a first binding domain may include a peptide having binding specificity for bone, and a second binding domain that comprises a peptide having binding specificity for a selected pharmaceutically active agent.

Example 4

In this example, illustrated are method embodiments that include the following: (a) a method for manufacturing a coated bone implant; (b) a method of coating a surface of bone by a process selected from the group that includes delivery of a pharmaceutically active agent to the coated bone surface, localizing a pharmaceutically active agent to the coated bone surface, recruiting a pharmaceutically active agent to the coated bone surface, and a combination thereof; (c) a delivery system for bone that includes a coating composition which, when applied to bone, provides a benefit selected from the group including delivery of a pharmaceutically active agent to the coated bone surface, localizing a pharmaceutically active agent to the coated bone surface, recruiting a pharmaceutically active agent to the coated bone surface, and a combination thereof; (d) a method of promoting a process selected from the group that includes osteoinduction, osteoconduction, osteogenesis, and a combination thereof, wherein the method comprises coating a bone surface with a coating composition embodiment.

The method and delivery system embodiments comprise contacting at least one surface of bone with an effective amount of a coating composition embodiment under conditions suitable to produce a coating on the surface. The coating composition comprises a coating composition selected from the group including of at least one binding domain that includes a peptide having binding specificity for bone; at least one binding domain including a peptide having binding specificity for bone and at least one binding domain that includes a peptide having binding specificity for a pharmaceutically active agent wherein the at least one binding domain comprising a peptide having binding specificity for bone and at least one binding domain that includes a peptide having binding specificity for a pharmaceutically active agent are coupled together; in one embodiment, via a linker; and a combination thereof. The at least one binding domain comprising a peptide having binding specificity for bone may include two or more peptides linked by a multi-branched linker, for one embodiment, including the same amino acid sequence, such as SEQ ID NO:40, or may comprise two or more peptides, each including a different amino acid sequence, such as one peptide that comprises the amino acid sequence of SEQ ID NO:41, and another peptide comprises the amino acid sequence of SEQ ID NO:42.

The at least one binding domain including a peptide having binding specificity for a pharmaceutically active agent comprises a single type such as two or more peptides, each having binding specificity for a single type of pharmaceutically active agent, such as, for example, cells, or may comprise a plurality of types such as two or more peptides. Each type comprises a peptide having binding specificity for a different pharmaceutically active agent from another type; such as a first peptide having binding specificity for a pharmaceutically active agent comprising cells, a second peptide having binding specificity for a growth factor, or a first peptide having binding specificity for a first growth factor and a second peptide having binding specificity for a second growth factor.

In these methods, when coating composition is contacted with the at least one surface of bone to be coated, either (a) the at least one peptide having binding specificity for a pharmaceutically active agent is bound to the pharmaceutically active agent for which it has binding specificity (for example, capture of pharmaceutically active agent of exogenous origin by peptide); or (b) the at least one peptide having binding specificity for a pharmaceutically active agent is not yet bound to the pharmaceutically active agent for which it has binding specificity such as, for example, when a bone coated with the coating composition is implanted. With respect to the latter, in a further step of coating, the coated bone is then contacted with a sufficient amount of pharmaceutically active agent in vitro or in vivo, for which the at least one peptide has binding specificity, under conditions suitable so that the pharmaceutically active agent binds to the at least one peptide. In one example, coated bone may be contacted in vitro with a pharmaceutically active agent, cells and/or growth factor, which is autologous or from a donor, allogeneic or xenogeneic, for the pharmaceutically active agent can bind to the peptide including the coated surface of the bone, and subsequently the bone is implanted. In another example, coated bone may be implanted, wherein in vivo the coated bone is contacted with and binds to a pharmaceutically active agent such as cells and/or growth factor which is endogenously produced by the individual receiving the coated bone. By binding one or more pharmaceutically active agents to coated bone, promoted is potential for capability to stimulate one or more of osteoinduction, osteoconduction, and osteogenesis.

Conventional processes may be used to apply the coating composition embodiments to the one or more surfaces of bone to be coated by contacting the coating composition with the one or more surfaces. Depending on the formulation of bone to be coated, usable processes include, but are not limited to, mixing, dipping, brushing, spraying, and vapor deposition. For example, a solution or suspension including the coating composition may be applied through the spray nozzle of a spraying device, creating droplets that coat the surface of bone to be coated. The coated bone is allowed to dry, and for some embodiments, is then further processed prior to use by washing in a solution of water or isotonic buffer to remove excess coating composition, followed by sterilization. Alternatively, the coating composition embodiments and the medical device embodiments may each be sterilized prior to the process of coating, and the process performed under aseptic conditions.

Another process for applying coating composition embodiments to one or more surfaces of bone to be coated comprises dipping the surface of bone to be coated into a liquid, solution or suspension, aqueous or solvent, containing coating composition in an amount effective to coat bone. For example, the surface is dipped or immersed into a bath containing the coating composition embodiment. Suitable conditions for applying the coating composition include allowing the surface to be coated to remain in contact with the liquid containing the coating composition for a suitable period of time, ranging from about 5 minutes to about 12 hours. In another embodiment, times ranged from 15 minutes to 60 minutes. Suitable temperatures ranged from 10° C. to about 50° C.; for some embodiments and ranged from room temperature to 37° C. for other embodiments. The coated bone was then further processed, as necessary for use by washing or sterilization.

Another process embodiment for applying the coating composition to bone to be coated included formulating the coating composition embodiment in a dry powder via air drying or lyophilizing the coating composition embodiment which was then mixed with the bone to produce a bone formulation that includes a solid, powder, paste, filler, binder, gel, sponge, implant, graft, and a combination thereof. However, these illustrative processes for applying a coating composition embodiment to bone are not exclusive, as other coating and stabilization methods may be employed. Additionally, in a method embodiment, a coat including the coating composition may be stabilized, for example, by air drying. However, these treatments are not exclusive, and other coating and stabilization methods may be employed. Suitable coating and stabilization methods include, for example, the at least one surface of bone to be coated with the coating composition embodiment may be pre-treated prior to the coating step so as to enhance one or more of: the binding of peptide having binding specificity for bone to be coated; and the consistency and uniformity of the coating. For example, such pretreatment may include etching or acid-treating the bone surface to be coated in enhancing the binding of a peptide having binding specificity for bone by enhancing hydrophilic interactions, or the molecular adhesiveness, between the bone surface and amino acids of the peptide.

Example 5

Illustrated are examples of composition embodiments including at least one peptide embodiment having binding specificity for bone, coupled to at least one peptide embodiment having binding specificity for a pharmaceutically active agent; and may further include pharmaceutically active agent bound thereto. This example includes several composition embodiments, using peptide embodiments having binding specificity for bone disclosed herein, each composition including formula I:

$X_1$-J-$X_2$-P, wherein $X_1$ is a peptide (i) comprising from about 5 amino acids to about 50 amino acids and for other embodiments from about 10 amino acids to about 25 amino acids, and for other embodiments, from about 10 amino acids to about 15 amino acids; (ii) comprising a domain or motif that includes 3 or more large aromatic amino acid residues, one or more of Phe, Trp, Tyr, within a sequence including the first 10 contiguous amino acids from the N-terminal end of the peptide and, for some embodiments, within the first 8, and for other embodiments, within the first 5, amino acids from the N-terminus of the amino acid sequence of the peptide; (iii) having binding specificity for bone; and (iv) lacking a collagen-derived sequence having a cell-binding domain characterized by the sequence Gly-Ile-Ala;

J comprises a linker;

$X_2$ comprises a peptide (i) comprising an amino acid sequence having from about 3 amino acids to about 50 amino acids, and for some embodiments, from about 10 amino acids to about 25 amino acids, and for some embodiments, from about 10 amino acids to about 15 amino acids; and (ii) having binding specificity for a pharmaceutically active agent; and P is absent, or comprises a pharmaceutically active agent.

Using conventional methods for peptide synthesis, composition embodiments were synthesized. The composition embodiments comprised the amino acid sequences comprising SEQ ID NOs:133-136 composition, and corresponding SEQ ID NOs:137-140. SEQ ID NOs:137-140 include an extra linker sequence at the C-terminus, to which was linked biotin for binding experiments described herein. Also synthesized were compositions of the invention comprising SEQ ID NOs: 141 & 142. As shown in Table 7, the underlined amino acid sequences include the denoted $X_1$ and $X_2$ amino acid sequences, and J is represented by the amino acid sequences, without underlining, joining the underlined sequences.

TABLE 7

| | SEQ ID NO: 133 |
|---|---|
| SWWGFWNGSAAPVWSRGSSESAGAWEAFSSLSGSRV | |
| $X_1$ SEQ ID NO: 41    J    $X_2$ SEQ ID NO: 91 | |
| | SEQ ID NO: 137 |
| SWWGFWNGSAAPVWSRGSSESAGAWEAFSSLSGSRVGSSGK | |
| | SEQ ID NO: 134 |
| SWWGFWNGSAAPVWSRGSSGAGAWEAFSSLSGSRV | |
| $X_1$ SEQ ID NO: 41    J    $X_2$ SEQ ID NO: 91 | |
| | SEQ ID NO: 138 |
| SWWGFWNGSAAPVWSRGSSGAGAWEAFSSLSGSRVGSSGK | |
| | SEQ ID NO: 135 |
| SWWGFWNGSAAPVWSRGSSGAGALGFPLKGEVVEGWA | |
| $X_1$ SEQ ID NO: 41    J    $X_2$ SEQ ID NO: 118 | |
| | SEQ ID NO: 139 |
| SWWGFWNGSAAPVWSRGSSGAGALGFPLKGEVVEGWAGSSGK | |
| | SEQ ID NO: 136 |
| SFGSWWWGSGAASSRGSSGGGALGFPLKGEVVEGWA | |
| $X_1$ SEQ ID NO: 42    J    $X_2$ SEQ ID NO: 118 | |
| | SEQ ID NO: 140 |
| SFGSWWWGSGAASSRGSSGGGALGFPLKGEVVEGWAGSSGK | |
| | SEQ ID NO: 141 |
| SFGSWWWGSGAASSRG-(PEG10)-GGGAWEAFSSLSGSRVGSSGK | |
| $X_1$ SEQ ID NO: 42    J    $X_2$ SEQ ID NO: 91 | |
| | SEQ ID NO: 142 |
| SFGSWWWGSGAASSRG-(PEG10)-AGAWEAFSSLSGSRVGSSGK | |

Relative binding strength embodiments of the compositions to bone, also used as a measure of binding specificity, were determined by testing serial dilutions of the composition for binding to bone, as described in Example 1 Section B. Plotting the absorbance observed across the concentration range for each composition yielded a binding curve and rough dissociation constant of the composition for bone. Similar to a peptide having binding specificity for bone from which the composition is made, one property of the composition embodiments is that they bind to bone with binding specificity as measured by an EC50 of less than or equal to about 10 μM, and for some embodiments, in the nanomolar range (<1 μM). Using the methods outlined in Example 1B herein, assayed were the relative binding strengths of four illustrative composition embodiments which include the amino acid sequences shown in SEQ ID NOs: 137, 138, 139, 140, 141 &

142, see Table 7, and synthesized to include a C-terminal amino linker which was biotinylated to facilitate determination of the relative binding strengths to bone. Shown in Table 8 are the relative binding strengths of composition embodiments to bone, as represented by DBM, expressed as EC50 (in μM).

TABLE 8

Binding specificity for bone

| SEQ ID NO: | EC50 (μM) |
|---|---|
| 137 | <0.5 |
| 138 | <0.1 |
| 139 | <0.5 |
| 140 | <0.5 |
| 141 | <0.5 |
| 142 | <0.5 |

As shown in Table 8, composition embodiments demonstrate a binding specificity to bone in the nanomolar range (<1 μM).

Composition embodiments, described herein, have an ability, while bound to bone via peptide having binding specificity to bone, to also bind a pharmaceutically active agent. In this example, the pharmaceutically active agent is a growth factor, and more particularly, BMP-2. A binding assay was performed using ELISA; and the resultant absorbance observed across the concentration range of pharmaceutically active agent yielded a binding curve and rough dissociation constant of the composition which were used to calculate an EC50. Appropriate controls, including absence of the composition, were included in the assay.

As a specific example, DBM was placed in a microtiter plate at a concentration of 3 mg equivalents per well, and then the wells and DBM were blocked with buffer containing 1% BSA for 1 hour at room temperature. The buffer containing 1% BSA was then aspirated from each well, and added to each of the wells was 100 μl of buffer containing 10 μM of the respective composition embodiments. The microtiter plates were incubated for 1 hour at room temperature on a plate shaker. The DBM was then allowed to settle, and the buffer was then aspirated from the wells. The DBM was washed three times with buffer-T, and then serial dilutions of BMP-2 were added to the wells in 100 μl of buffer. The microtiter plates were then incubated for 1 hour at room temperature on a plate shaker. The DBM, having composition bound thereto, was then allowed to settle, and then buffer was aspirated from the wells. The DBM-composition combination was washed three times with buffer-T. Commercial murine anti-BMP-2 antibody was diluted 1:1000 in buffer containing 1% BSA, and 100 μl was added per well. The plates were incubated for 30 minutes at room temperature on a plate shaker, and then the wash step was repeated. Commercial anti-mouse antibody labeled with alkaline phosphatase was diluted 1:1000 in buffer containing 1% BSA, and 100 μl was added per well. The plates were incubated for 30 minutes at room temperature on a plate shaker, and then the wash step was repeated. Added to each well was 200 μl of substrate pNPP, and the plates were incubated at room temperature on a plate shaker to develop the assay. 100 μl of solution was removed from each well and added to a respective well of a new microtiter plate which was then read on a spectrophotometer and the absorbance was recorded at 405 nm. An estimate of the relative affinity, binding specificity, EC50 of the composition for pharmaceutically active agent can be made by determining the concentration of peptide that provides one-half the maximal signal in the assay.

Table 9 shows the results, expressed as EC50 in nM, of six illustrative compositions comprising the amino acid sequences: shown in SEQ ID NOs: 133, 134, 135, & 136, and as represented by corresponding SEQ ID NOs: 137, 138, 139, & 140, respectively; and shown in SEQ ID NOs: 141 & 142. Each composition was first bound to bone, and then assayed for binding to pharmaceutically active agent, as represented by BMP-2.

TABLE 9

Binding specificities for BMP of bone-bound compositions

| SEQ ID NO: | EC50 (nM) |
|---|---|
| 137 | <10 |
| 138 | <10 |
| 139 | <10 |
| 140 | <10 |
| 141 | <10 |
| 142 | <10 |

Thus, the results in Table 9 demonstrate that when the composition embodiments were bound to bone, via $X_1$, unexpectedly maintained is the ability of the composition to bind specifically with an EC50 in the nanomolar range to a pharmaceutically active agent, via $X_2$. Also demonstrated are: (a) a composition that comprised $X_1$ coupled to $X_2$; (b) a composition comprised of $X_1$ coupled to $X_2$, and including P bound to $X_2$; (c) bone coated by a composition that comprises $X_1$ coupled to $X_2$; and (d) bone coated by a composition that comprises $X_1$ coupled to $X_2$, and comprising P bound to $X_2$.

Example 6

Based on the amino acid sequence of the peptide embodiments comprising a binding domain with binding specificity for bone, polynucleotides, nucleic acid molecules, encoding such a peptide or variants thereof as described herein may be synthesized or constructed, and that such a peptide may be produced by recombinant DNA technology as a method of manufacture such as in culture and/or in vivo production by introducing such polynucleotides in vivo. For example, more than one polynucleotide sequence can encode a peptide embodiment, and that such polynucleotides may be synthesized on the bases of triplet codons known to encode the amino acids of the peptide, third base degeneracy, and selection of triplet codon usage used by a cell-free expression system or the host cell, typically a prokaryotic cell or eukaryotic cell such as bacterial cells such as E. coli; yeast cells; mammalian cells; avian cells; amphibian cells; plant cells; fish cells; and insect cells; whether located in vitro or in vivo in which expression is desired.

For purposes of illustration only, and not limitation, provided are SEQ ID NO:126-132 which are polynucleotides encoding amino acid sequences of SEQ ID NO:5, 13, 37, 30, 41, 43, and 4 from which, codon usage generally applies to polynucleotides encoding a peptide embodiments which has binding specificity for bone. Thus, for example, using SEQ ID NO:126 in relation to SEQ ID NO: 5, one skilled in the art could readily construct a polynucleotide encoding variants of the amino acid sequence illustrated in SEQ ID NO:5, or deduce the polynucleotide sequence encoding an amino acid sequence illustrated as SEQ ID NO:6. In one embodiment according to the invention, a polynucleotide encoding an amino acid sequence of a peptide having binding specificity for bone such as SEQ ID NO:5 comprises a nucleic acid molecule encoding a peptide consisting of the amino acid sequence such as SEQ ID NO:5 or an amino acid sequence having at least 95% identity and for other embodiments, at least 90% identity with the amino acid sequence such as with SEQ ID NO:5, provided the encoded peptide substantially retains binding specificity for bone.

One illustrative embodiment comprises a recombinant vector containing a polynucleotide encoding a binding domain including a peptide having binding specificity for bone for use in accordance with embodiments of the present invention; and its use for the recombinant production of a peptide having binding specificity for bone. In one example, the polynucleotide may be added to a cell-free expression system known in the art for producing peptides or polypeptides. In another example, the polynucleotide may be positioned in a prokaryotic expression vector so that when the peptide is produced in bacterial host cells, it is produced as a fusion protein with other amino acid sequences which assist in purification of the peptide; or as recombinantly coupled to a surface-binding domain. For example, there are sequences which, as part of a fusion protein with a peptide desired to be expressed, facilitate production in inclusion bodies found in the cytoplasm of the prokaryotic cell used for expression and/or assists in purification of fusion proteins containing such sequence. Inclusion bodies may be separated from other prokaryotic cellular components by methods known in the art to include denaturing agents, and fractionation, such as centrifugation, column chromatography, and the like. In another example, there are commercially available vectors into which is inserted a desired nucleic acid sequence of interest to be expressed as a protein or peptide such that upon expression, the gene product also contains a plurality of terminal histidine residues, "His tags" that can be utilized in the purification of the gene product using conventional methods.

A nucleic acid sequence encoding a binding domain including a peptide having binding specificity for bone can be inserted into, and become part of a, nucleic acid molecule including a plasmid, or vectors other than plasmids; and other expression systems can be used including, but not limited to, bacteria transformed with a bacteriophage vector, or cosmid DNA; yeast containing yeast vectors; fungi containing fungal vectors; insect cell lines infected with virus such as baculovirus); and mammalian cell lines having introduced therein (e.g., transfected or electroporated with) plasmid or viral expression vectors, or infected with recombinant virus such as vaccinia virus, adenovirus, adeno-associated virus, and retrovirus. Successful expression of the peptide requires that either the recombinant nucleic acid molecule including the encoding sequence of the peptide, or the vector itself, contain the necessary control elements for transcription and translation which is compatible with, and recognized by the particular host system used for expression.

Using methods known in the art of molecular biology, including methods described above, various promoters and enhancers can be incorporated into the vector or the recombinant nucleic acid molecule including the encoding sequence to increase the expression of the peptide, provided that the increased expression of the peptide is compatible with (for example, non-toxic to) the particular host cell system used. The selection of the promoter will depend on the expression system used. Promoters vary in strength, i.e., ability to facilitate transcription. Generally, for the purpose of expressing a cloned gene, it is desirable to use a strong promoter in order to obtain a high level of transcription of the gene and expression into gene product. For example, bacterial, phage, or plasmid promoters known in the art from which a high level of transcription has been observed in a host cell system comprising $E.$ $coli$ include the lac promoter, trp promoter, T7 promoter, recA promoter, ribosomal RNA promoter, the P.sub.R and P.sub.L promoters, lacUV5, ompF, bla, lpp, and the like, may be used to provide transcription of the inserted nucleotide sequence encoding the synthetic peptide. Commonly used mammalian promoters in expression vectors for mammalian expression systems are the promoters from mammalian viral genes. Examples include the SV40 early promoter, mouse mammary tumor virus LTR promoter, adenovirus major late promoter, herpes simplex virus promoter, and the CMV promoter.

In the case where expression of the peptide may be lethal or detrimental to the host cells, the host cell strain/line and expression vectors may be chosen such that the action of the promoter is inhibited until specifically induced. For example, in certain operons the addition of specific inducers is necessary for efficient transcription of the inserted DNA (e.g., the lac operon is induced by the addition of lactose or isopropylthio-beta-D-galactoside ("IPTG"); trp operon is induced when tryptophan is absent in the growth media; and tetracycline can be use in mammalian expression vectors having a tet sensitive promoter). Thus, expression of the peptide may be controlled by culturing transformed or transfected cells under conditions such that the promoter controlling the expression from the encoding sequence is not induced, and when the cells reach a suitable density in the growth medium, the promoter can be induced for expression from the encoding sequence. Other control elements for efficient gene transcription or message translation are well known in the art to include enhancers, transcription or translation initiation signals, transcription termination and polyadenylation sequences, and the like.

The foregoing description of the specific embodiments of the present invention have been described in detail for purposes of illustration. In view of the descriptions and illustrations, others skilled in the art can, by applying, current knowledge, readily modify and/or adapt the present invention for various applications without departing from the basic concept of the present invention; and thus, such modifications and/or adaptations are intended to be within the meaning and scope of the appended claims.

What is claimed is:

1. A coating composition comprising a peptide that binds to bone coupled to a peptide that binds to a pharmaceutically active agent,
    wherein the peptide that binds to bone is no more than about 50 amino acid residues in length and comprises an amino acid sequence that is at least 95% identical to any one of SEQ ID NOs: 1-45, and
    wherein the peptide that binds to a pharmaceutically active agent is about 3 to about 50 amino acid residues in length and has binding specificity for a pharmaceutically active agent.

2. The coating composition of claim 1, wherein the peptide that binds to bone is coupled to the peptide that binds to a pharmaceutically active agent by a linker.

3. The coating composition of claim 1, wherein the peptide that binds to bone comprises one or more of SEQ ID NOs: 1-45.

4. The coating composition of claim 1, wherein the peptide that binds to a pharmaceutically active agent comprises one or more of SEQ ID NOs: 48-125.

5. A bone-tropic peptide which is no more than about 50 amino acid residues in length and comprises an amino acid sequence that is at least 95% identical to any one of SEQ ID NOs: 1-45.

6. A method for enhancing one or more of osteoinduction, osteoconduction, and osteogenesis, comprising applying to a bone or a bone implant the coating composition of claim 1.

7. The method of claim 6, wherein the peptide that binds to a pharmaceutically active agent comprises one or more of SEQ ID NOs: 48-118 and is bound to a BMP.

8. The method of claim 6, wherein the peptide that binds to a pharmaceutically active agent comprises one or more of SEQ ID NO: 119-121 and is bound to a stem cell or osteoblast.

9. The method of claim 6, wherein the peptide that binds to a pharmaceutically active agent comprises SEQ ID NO: 122 and is bound to vitamin D.

10. The method of claim 6, wherein the peptide that binds to a pharmaceutically active agent comprises SEQ ID NO: 123 and is bound to paclitaxel.

11. The method of claim 6, wherein the peptide that binds to a pharmaceutically active agent comprises SEQ ID NO: 124 and is bound to human growth hormone.

12. The bone-tropic peptide of claim 5, comprising any of SEQ ID NOs: 1-45.

13. The coating composition of claim 1, wherein the peptide that binds to a pharmaceutically active agent is selected from SEQ ID NOs: 48-118 and is bound to a BMP, the peptide that binds to a pharmaceutically active agent is selected from SEQ ID NO: 119-121 and is bound to a stem cell or osteoblast, the peptide that binds to a pharmaceutically active agent is SEQ ID NO: 122 and is bound to vitamin D, the peptide that binds to a pharmaceutically active agent is SEQ ID NO: 123 and is bound to paclitaxel, or the peptide that binds to a pharmaceutically active agent is SEQ ID NO: 124 and is bound to human growth hormone.

14. The coating composition of claim 2, wherein the linker is a synthetic polymer or a natural polymer.

15. Bone having applied thereon a coating composition, the coating composition comprising a peptide that binds to bone coupled to a peptide that binds to a pharmaceutically active agent,
    wherein the peptide that binds to bone is no more than about 50 amino acid residues in length and comprises an amino acid sequence that is at least 95% identical to any one of SEQ ID NOs: 1-45, and
    wherein the peptide that binds to a pharmaceutically active agent is about 3 to about 50 amino acid residues in length and has binding specificity for a pharmaceutically active agent.

16. The bone of claim 15, wherein the peptide that binds to a pharmaceutically active agent comprises any of SEQ ID NOs: 48-125.

17. The bone of claim 15, wherein the peptide that binds to a pharmaceutically active agent is selected from SEQ ID NOs: 48-118 and is bound to a BMP, the peptide that binds to a pharmaceutically active agent is selected from SEQ ID NO: 119-121 and is bound to a stem cell or osteoblast, the peptide that binds to a pharmaceutically active agent is SEQ ID NO: 122 and is bound to vitamin D, the peptide that binds to a pharmaceutically active agent is SEQ ID NO: 123 and is bound to paclitaxel, or the peptide that binds to a pharmaceutically active agent is SEQ ID NO: 124 and is bound to human growth hormone.

18. A delivery system for delivering pharmaceutically active agents to bone comprising a coating composition and a contactor system,
    wherein the coating composition comprises a peptide that binds to bone coupled to a peptide that binds to a pharmaceutically active agent,
    wherein the peptide that binds to bone is no more than about 50 amino acid residues in length and comprises an amino acid sequence that is at least 95% identical to any one of SEQ ID NOs: 1-45, and
    wherein the peptide that binds to a pharmaceutically active agent is about 3 to about 50 amino acid residues in length and has binding specificity for a pharmaceutically active agent.

19. The delivery system of claim 18, wherein the peptide that binds to a pharmaceutically active agent comprises any of SEQ ID NOs: 48-125.

20. The delivery system of claim 18, wherein the peptide that binds to a pharmaceutically active agent is selected from SEQ ID NOs: 48-118 and is bound to a BMP, the peptide that binds to a pharmaceutically active agent is selected from SEQ ID NO: 119-121 and is bound to a stem cell or osteoblast, the peptide that binds to a pharmaceutically active agent is SEQ ID NO: 122 and is bound to vitamin D, the peptide that binds to a pharmaceutically active agent is SEQ ID NO: 123 and is bound to paclitaxel, or the peptide that binds to a pharmaceutically active agent is SEQ ID NO: 124 and is bound to human growth hormone.

* * * * *

SEQUENCE LISTING

<160> NUMBER OF SEQ ID NOS: 142

<210> SEQ ID NO 1
<211> LENGTH: 13
<212> TYPE: PRT
<213> ORGANISM: Artificial
<220> FEATURE:
<223> OTHER INFORMATION: synthesized -continued

```
<400> SEQUENCE: 1

Phe Tyr Ser Ile Phe Phe Pro Gln Met Gly Gly Ser Met
1               5                   10

<210> SEQ ID NO 2
<211> LENGTH: 13
<212> TYPE: PRT
<213> ORGANISM: Artificial
<220> FEATURE:
<223> OTHER INFORMATION: synthesized

<400> SEQUENCE: 2

Phe Ser Gly Trp Phe Leu Pro Trp Glu Gly Arg Ser Glu
1               5                   10

<210> SEQ ID NO 3
<211> LENGTH: 13
<212> TYPE: PRT
<213> ORGANISM: Artificial
<220> FEATURE:
<223> OTHER INFORMATION: synthesized

<400> SEQUENCE: 3

Phe Tyr Trp Pro Ser Phe Asn Ser Gly Asn Ser Leu Trp
1               5                   10

<210> SEQ ID NO 4
<211> LENGTH: 13
<212> TYPE: PRT
<213> ORGANISM: Artificial
<220> FEATURE:
<223> OTHER INFORMATION: synthesized

<400> SEQUENCE: 4

Phe Ser Trp Phe Ser Tyr Pro Ser Gln Leu Trp Met Glu
1               5                   10

<210> SEQ ID NO 5
<211> LENGTH: 13
<212> TYPE: PRT
<213> ORGANISM: Artificial
<220> FEATURE:
<223> OTHER INFORMATION: synthesized

<400> SEQUENCE: 5

Ile Phe Ser Thr Trp Asn Pro Trp Ser Pro Tyr Ser Val
1               5                   10

<210> SEQ ID NO 6
<211> LENGTH: 13
<212> TYPE: PRT
<213> ORGANISM: Artificial
<220> FEATURE:
<223> OTHER INFORMATION: synthesized

<400> SEQUENCE: 6

Phe Ser Trp Phe Gly Ser His Leu Leu Ser Gly Gly Ser
1               5                   10

<210> SEQ ID NO 7
<211> LENGTH: 13
<212> TYPE: PRT
<213> ORGANISM: Artificial
<220> FEATURE:
<223> OTHER INFORMATION: synthesized
```

```
<400> SEQUENCE: 7

Phe Ala Thr Phe Phe Gly Gly Ser Val Glu Lys Phe Trp
1               5                   10

<210> SEQ ID NO 8
<211> LENGTH: 13
<212> TYPE: PRT
<213> ORGANISM: Artificial
<220> FEATURE:
<223> OTHER INFORMATION: synthesized

<400> SEQUENCE: 8

Trp Asn Tyr Gly Asp Val Gly Arg Trp Trp Asp Trp Gln
1               5                   10

<210> SEQ ID NO 9
<211> LENGTH: 13
<212> TYPE: PRT
<213> ORGANISM: Artificial
<220> FEATURE:
<223> OTHER INFORMATION: synthesized

<400> SEQUENCE: 9

Trp Trp Gly Phe Trp Asn Gly Ser Ala Ala Pro Val Trp
1               5                   10

<210> SEQ ID NO 10
<211> LENGTH: 19
<212> TYPE: PRT
<213> ORGANISM: Artificial
<220> FEATURE:
<223> OTHER INFORMATION: synthesized

<400> SEQUENCE: 10

Ser Ser Leu Leu Tyr Asn Trp Leu Asp Asn Thr Arg Gln Met Phe Leu
1               5                   10                  15

Pro Glu Ser

<210> SEQ ID NO 11
<211> LENGTH: 17
<212> TYPE: PRT
<213> ORGANISM: Artificial
<220> FEATURE:
<223> OTHER INFORMATION: synthesized

<400> SEQUENCE: 11

Trp Cys Val Trp Gly Leu Gly Ser Gly Cys Ala Gly Gly Ala Ala Val
1               5                   10                  15

Gly

<210> SEQ ID NO 12
<211> LENGTH: 17
<212> TYPE: PRT
<213> ORGANISM: Artificial
<220> FEATURE:
<223> OTHER INFORMATION: synthesized

<400> SEQUENCE: 12

Trp Ser Pro Asp Val Leu Arg Trp Pro Trp Trp Ala Ser Gly Ser Ser
1               5                   10                  15

Glu
```

```
<210> SEQ ID NO 13
<211> LENGTH: 17
<212> TYPE: PRT
<213> ORGANISM: Artificial
<220> FEATURE:
<223> OTHER INFORMATION: synthesized

<400> SEQUENCE: 13

Phe Trp Ser Ala Asp Phe Ser Ala Glu Asp Ala Ser Ala Trp Trp Gly
1               5                   10                  15

Trp

<210> SEQ ID NO 14
<211> LENGTH: 12
<212> TYPE: PRT
<213> ORGANISM: Artificial
<220> FEATURE:
<223> OTHER INFORMATION: synthesized

<400> SEQUENCE: 14

Phe Gly Ser Trp Trp Trp Gly Ser Gly Ala Ala Ser
1               5                   10

<210> SEQ ID NO 15
<211> LENGTH: 17
<212> TYPE: PRT
<213> ORGANISM: Artificial
<220> FEATURE:
<223> OTHER INFORMATION: synthesized

<400> SEQUENCE: 15

Phe Ser Pro Asp Phe Leu Ser Ser Trp Trp Gln Thr His Ala Gly Arg
1               5                   10                  15

Phe

<210> SEQ ID NO 16
<211> LENGTH: 17
<212> TYPE: PRT
<213> ORGANISM: Artificial
<220> FEATURE:
<223> OTHER INFORMATION: synthesized

<400> SEQUENCE: 16

Ser Phe Phe Ser Pro Tyr Ser Ala Phe Ser Trp Val Glu Ser Ala
1               5                   10                  15

Arg

<210> SEQ ID NO 17
<211> LENGTH: 17
<212> TYPE: PRT
<213> ORGANISM: Artificial
<220> FEATURE:
<223> OTHER INFORMATION: synthesized

<400> SEQUENCE: 17

Trp Ser Ser Phe Phe Pro Leu Gly Phe Ser Ser Trp Ser Gly Ser Val
1               5                   10                  15

Pro

<210> SEQ ID NO 18
<211> LENGTH: 17
<212> TYPE: PRT
<213> ORGANISM: Artificial
<220> FEATURE:
<223> OTHER INFORMATION: synthesized
```

-continued

```
<400> SEQUENCE: 18

Phe Ser Phe Ser Ser Leu Pro Ala Trp Ser Ser Phe Trp Pro Thr Ser
1               5                   10                  15

Thr

<210> SEQ ID NO 19
<211> LENGTH: 14
<212> TYPE: PRT
<213> ORGANISM: Artificial
<220> FEATURE:
<223> OTHER INFORMATION: synthesized

<400> SEQUENCE: 19

Phe Ser Phe Leu Ser Ser Ala Val Glu Arg Ile Tyr Gly Ala
1               5                   10

<210> SEQ ID NO 20
<211> LENGTH: 17
<212> TYPE: PRT
<213> ORGANISM: Artificial
<220> FEATURE:
<223> OTHER INFORMATION: synthesized

<400> SEQUENCE: 20

Thr Trp Gln Ser Tyr Leu Asp Leu Trp Gly Trp Thr Pro Thr Pro Ser
1               5                   10                  15

Leu

<210> SEQ ID NO 21
<211> LENGTH: 17
<212> TYPE: PRT
<213> ORGANISM: Artificial
<220> FEATURE:
<223> OTHER INFORMATION: synthesized

<400> SEQUENCE: 21

Trp Pro Gly Ser Gly Trp Trp Trp Ser Glu Gly Leu Gln Arg Arg Glu
1               5                   10                  15

Val

<210> SEQ ID NO 22
<211> LENGTH: 17
<212> TYPE: PRT
<213> ORGANISM: Artificial
<220> FEATURE:
<223> OTHER INFORMATION: synthesized

<400> SEQUENCE: 22

Trp Pro Met Pro Trp Trp Ser Glu Trp Ala Ser Leu His Gly Gly Lys
1               5                   10                  15

Trp

<210> SEQ ID NO 23
<211> LENGTH: 17
<212> TYPE: PRT
<213> ORGANISM: Artificial
<220> FEATURE:
<223> OTHER INFORMATION: synthesized

<400> SEQUENCE: 23

Trp Trp Pro His Val Ser Gly Val Tyr Gly Ser Leu Pro Trp Gly Pro
1               5                   10                  15

Gly
```

```
<210> SEQ ID NO 24
<211> LENGTH: 17
<212> TYPE: PRT
<213> ORGANISM: Artificial
<220> FEATURE:
<223> OTHER INFORMATION: synthesized

<400> SEQUENCE: 24

Leu Gly Thr Phe Trp Ser Ser Val Trp Arg Gly Val Asp Ala Gly Gly
1               5                   10                  15

Glu

<210> SEQ ID NO 25
<211> LENGTH: 17
<212> TYPE: PRT
<213> ORGANISM: Artificial
<220> FEATURE:
<223> OTHER INFORMATION: synthesized

<400> SEQUENCE: 25

Val Gly Trp Gly Asp Trp Trp Lys Ser Gly Ser Val Trp Gln Gly Ala
1               5                   10                  15

Leu

<210> SEQ ID NO 26
<211> LENGTH: 13
<212> TYPE: PRT
<213> ORGANISM: Artificial
<220> FEATURE:
<223> OTHER INFORMATION: synthesized

<400> SEQUENCE: 26

Phe Gly His Phe Glu Trp Pro Val Leu Gly Gln Trp Lys
1               5                   10

<210> SEQ ID NO 27
<211> LENGTH: 13
<212> TYPE: PRT
<213> ORGANISM: Artificial
<220> FEATURE:
<223> OTHER INFORMATION: synthesized

<400> SEQUENCE: 27

Phe Leu Ser Ala Ser Met Pro Tyr Leu Gln Ala Trp Ala
1               5                   10

<210> SEQ ID NO 28
<211> LENGTH: 13
<212> TYPE: PRT
<213> ORGANISM: Artificial
<220> FEATURE:
<223> OTHER INFORMATION: synthesized

<400> SEQUENCE: 28

Phe Ser Tyr Phe Ser Ser Pro Ser Thr Trp Val Gln Trp
1               5                   10

<210> SEQ ID NO 29
<211> LENGTH: 19
<212> TYPE: PRT
<213> ORGANISM: Artificial
<220> FEATURE:
<223> OTHER INFORMATION: synthesized
```

<400> SEQUENCE: 29

Ser Ser Met Phe Lys Asp Phe Asp Ser Leu Val Lys Ser Trp Ser Gly
1               5                   10                  15

Arg Phe Ser

<210> SEQ ID NO 30
<211> LENGTH: 13
<212> TYPE: PRT
<213> ORGANISM: Artificial
<220> FEATURE:
<223> OTHER INFORMATION: synthesized

<400> SEQUENCE: 30

Phe Asp Ile Asp Trp Ser Gly Met Arg Ser Trp Trp Gly
1               5                   10

<210> SEQ ID NO 31
<211> LENGTH: 14
<212> TYPE: PRT
<213> ORGANISM: Artificial
<220> FEATURE:
<223> OTHER INFORMATION: synthesized

<400> SEQUENCE: 31

Ser Phe Asp Leu Ser Ala Phe Gly Ser Leu Trp Asp Arg Trp
1               5                   10

<210> SEQ ID NO 32
<211> LENGTH: 17
<212> TYPE: PRT
<213> ORGANISM: Artificial
<220> FEATURE:
<223> OTHER INFORMATION: synthesized

<400> SEQUENCE: 32

Phe Asp Arg Trp Gly Phe Gly Ala Gly Ala Trp Trp Asp Ser Val Ala
1               5                   10                  15

Ala

<210> SEQ ID NO 33
<211> LENGTH: 17
<212> TYPE: PRT
<213> ORGANISM: Artificial
<220> FEATURE:
<223> OTHER INFORMATION: synthesized

<400> SEQUENCE: 33

Val Ala Val Ala Ser Val Gly Ala Phe Trp Ser Gly Leu Ser Gly Trp
1               5                   10                  15

Ala

<210> SEQ ID NO 34
<211> LENGTH: 17
<212> TYPE: PRT
<213> ORGANISM: Artificial
<220> FEATURE:
<223> OTHER INFORMATION: synthesized

<400> SEQUENCE: 34

Phe Ser Trp Ser Ser Leu Ser Asp Ser Phe Gly Trp Gly Ser Ser Phe
1               5                   10                  15

Ser

```
<210> SEQ ID NO 35
<211> LENGTH: 17
<212> TYPE: PRT
<213> ORGANISM: Artificial
<220> FEATURE:
<223> OTHER INFORMATION: synthesized

<400> SEQUENCE: 35

Ser Leu Pro Ala Leu Pro Trp Gly Phe Pro Ser Trp Gln Gln Gly Trp
1               5                   10                  15
Leu

<210> SEQ ID NO 36
<211> LENGTH: 17
<212> TYPE: PRT
<213> ORGANISM: Artificial
<220> FEATURE:
<223> OTHER INFORMATION: synthesized

<400> SEQUENCE: 36

Phe Phe Thr His Phe Tyr Pro Pro Tyr Asp Val Arg Pro His Pro Pro
1               5                   10                  15
Ala

<210> SEQ ID NO 37
<211> LENGTH: 17
<212> TYPE: PRT
<213> ORGANISM: Artificial
<220> FEATURE:
<223> OTHER INFORMATION: synthesized

<400> SEQUENCE: 37

Trp Asp Phe Arg Ser Leu Arg Asp Trp Trp Pro Pro Ala Pro Ser Leu
1               5                   10                  15
Ser

<210> SEQ ID NO 38
<211> LENGTH: 17
<212> TYPE: PRT
<213> ORGANISM: Artificial
<220> FEATURE:
<223> OTHER INFORMATION: synthesized

<400> SEQUENCE: 38

Trp Leu Ser Gly Trp Ser Ala Gly Trp Gly Ser Val Ala Ala Pro Glu
1               5                   10                  15
Gly

<210> SEQ ID NO 39
<211> LENGTH: 17
<212> TYPE: PRT
<213> ORGANISM: Artificial
<220> FEATURE:
<223> OTHER INFORMATION: synthesized

<400> SEQUENCE: 39

Trp Ser Asn Gly Ala Trp Ala Lys Trp Trp Gly Val Ala Glu Glu Val
1               5                   10                  15
Gly

<210> SEQ ID NO 40
<211> LENGTH: 21
<212> TYPE: PRT
<213> ORGANISM: Artificial
```

```
<220> FEATURE:
<223> OTHER INFORMATION: synthesized

<400> SEQUENCE: 40

Ser Ile Phe Ser Thr Trp Asn Pro Trp Ser Pro Tyr Ser Val Ser Arg
1               5                   10                  15

Gly Ser Ser Gly Lys
            20

<210> SEQ ID NO 41
<211> LENGTH: 21
<212> TYPE: PRT
<213> ORGANISM: Artificial
<220> FEATURE:
<223> OTHER INFORMATION: synthesized

<400> SEQUENCE: 41

Ser Trp Trp Gly Phe Trp Asn Gly Ser Ala Ala Pro Val Trp Ser Arg
1               5                   10                  15

Gly Ser Ser Gly Lys
            20

<210> SEQ ID NO 42
<211> LENGTH: 20
<212> TYPE: PRT
<213> ORGANISM: Artificial
<220> FEATURE:
<223> OTHER INFORMATION: synthesized

<400> SEQUENCE: 42

Ser Phe Gly Ser Trp Trp Trp Gly Ser Gly Ala Ala Ser Ser Arg Gly
1               5                   10                  15

Ser Ser Gly Lys
            20

<210> SEQ ID NO 43
<211> LENGTH: 25
<212> TYPE: PRT
<213> ORGANISM: Artificial
<220> FEATURE:
<223> OTHER INFORMATION: synthesized

<400> SEQUENCE: 43

Ser Leu Gly Thr Phe Trp Ser Ser Val Trp Arg Gly Val Asp Ala Gly
1               5                   10                  15

Gly Glu Ser Arg Gly Ser Ser Gly Lys
            20                  25

<210> SEQ ID NO 44
<211> LENGTH: 21
<212> TYPE: PRT
<213> ORGANISM: Artificial
<220> FEATURE:
<223> OTHER INFORMATION: synthesized

<400> SEQUENCE: 44

Ser Phe Asp Ile Asp Trp Ser Gly Met Arg Ser Trp Trp Gly Ser Arg
1               5                   10                  15

Gly Ser Ser Gly Lys
            20

<210> SEQ ID NO 45
<211> LENGTH: 25
<212> TYPE: PRT
<213> ORGANISM: Artificial
```

```
<220> FEATURE:
<223> OTHER INFORMATION: synthesized

<400> SEQUENCE: 45

Ser Trp Asp Phe Arg Ser Leu Arg Asp Trp Trp Pro Pro Ala Pro Ser
1               5                   10                  15

Leu Ser Ser Arg Gly Ser Ser Gly Lys
            20                  25

<210> SEQ ID NO 46
<211> LENGTH: 13
<212> TYPE: PRT
<213> ORGANISM: Artificial
<220> FEATURE:
<223> OTHER INFORMATION: synthesized
<220> FEATURE:
<221> NAME/KEY: MISC_FEATURE
<222> LOCATION: (1)..(2)
<223> OTHER INFORMATION: Xaa comprises Phe, Trp, or Tyr
<220> FEATURE:
<221> NAME/KEY: MISC_FEATURE
<222> LOCATION: (3)..(3)
<223> OTHER INFORMATION: Xaa comprises any amino acid
<220> FEATURE:
<221> NAME/KEY: MISC_FEATURE
<222> LOCATION: (4)..(5)
<223> OTHER INFORMATION: Xaa comprises Phe, Trp, or Tyr
<220> FEATURE:
<221> NAME/KEY: MISC_FEATURE
<222> LOCATION: (6)..(12)
<223> OTHER INFORMATION: Xaa comprises any amino acid
<220> FEATURE:
<221> NAME/KEY: MISC_FEATURE
<222> LOCATION: (13)..(13)
<223> OTHER INFORMATION: Xaa comprises Phe, Trp, or Tyr

<400> SEQUENCE: 46

Xaa Xaa Xaa Xaa Xaa Xaa Xaa Xaa Xaa Xaa Xaa Xaa Xaa
1               5                   10

<210> SEQ ID NO 47
<211> LENGTH: 12
<212> TYPE: PRT
<213> ORGANISM: Artificial
<220> FEATURE:
<223> OTHER INFORMATION: synthesized
<220> FEATURE:
<221> NAME/KEY: MISC_FEATURE
<222> LOCATION: (1)..(1)
<223> OTHER INFORMATION: Xaa comprises Phe. Trp, or Tyr
<220> FEATURE:
<221> NAME/KEY: MISC_FEATURE
<222> LOCATION: (2)..(3)
<223> OTHER INFORMATION: Xaa is any amino acid
<220> FEATURE:
<221> NAME/KEY: MISC_FEATURE
<222> LOCATION: (4)..(6)
<223> OTHER INFORMATION: Xaa comprises Phe, Trp, or Tyr
<220> FEATURE:
<221> NAME/KEY: MISC_FEATURE
<222> LOCATION: (7)..(12)
<223> OTHER INFORMATION: Xaa is any amino acid

<400> SEQUENCE: 47

Xaa Xaa Xaa Xaa Xaa Xaa Xaa Xaa Xaa Xaa Xaa Xaa
1               5                   10

<210> SEQ ID NO 48
<211> LENGTH: 7
<212> TYPE: PRT
<213> ORGANISM: Artificial
<220> FEATURE:
<223> OTHER INFORMATION: synthesized
```

```
<220> FEATURE:
<221> NAME/KEY: MISC_FEATURE
<222> LOCATION: (1)..(1)
<223> OTHER INFORMATION: Xaa comprises Phe, Trp, or Tyr
<220> FEATURE:
<221> NAME/KEY: MISC_FEATURE
<222> LOCATION: (2)..(3)
<223> OTHER INFORMATION: Xaa is any amino acid
<220> FEATURE:
<221> NAME/KEY: MISC_FEATURE
<222> LOCATION: (5)..(5)
<223> OTHER INFORMATION: Xaa is any amino acid
<220> FEATURE:
<221> NAME/KEY: MISC_FEATURE
<222> LOCATION: (6)..(6)
<223> OTHER INFORMATION: Xaa comprises Ser, Thr, Ala, or Gly

<400> SEQUENCE: 48

Xaa Xaa Xaa Phe Xaa Xaa Leu
1               5

<210> SEQ ID NO 49
<211> LENGTH: 21
<212> TYPE: PRT
<213> ORGANISM: Artificial
<220> FEATURE:
<223> OTHER INFORMATION: synthesized

<400> SEQUENCE: 49

Ser Ser Asp Trp Gly Val Val Ala Ser Ala Trp Asp Ala Phe Glu Ala
1               5                   10                  15

Leu Asp Ala Ser Arg
            20

<210> SEQ ID NO 50
<211> LENGTH: 21
<212> TYPE: PRT
<213> ORGANISM: Artificial
<220> FEATURE:
<223> OTHER INFORMATION: synthesized

<400> SEQUENCE: 50

Ser Ser Gly Ala Asp Phe Gly Tyr Gly Ser Trp Val Ser Phe Ser Ala
1               5                   10                  15

Leu Ser Ala Ser Arg
            20

<210> SEQ ID NO 51
<211> LENGTH: 21
<212> TYPE: PRT
<213> ORGANISM: Artificial
<220> FEATURE:
<223> OTHER INFORMATION: synthesized

<400> SEQUENCE: 51

Ser Arg Gly Glu Ala Ser Gly Trp Glu Ala Phe Ser Ala Leu Glu Ala
1               5                   10                  15

Ala Val Val Ser Arg
            20

<210> SEQ ID NO 52
<211> LENGTH: 21
<212> TYPE: PRT
<213> ORGANISM: Artificial
<220> FEATURE:
<223> OTHER INFORMATION: synthesized
```

```
<400> SEQUENCE: 52

Ser Arg Ser Ser Asp Ser Ala Phe Ser Ser Phe Ser Ala Leu Glu Gly
1               5                   10                  15

Ser Val Val Ser Arg
            20

<210> SEQ ID NO 53
<211> LENGTH: 21
<212> TYPE: PRT
<213> ORGANISM: Artificial
<220> FEATURE:
<223> OTHER INFORMATION: synthesized

<400> SEQUENCE: 53

Ser Arg Asp Gly Ala Gly Ala Ala Ala Trp Gly Ala Phe Ser Ala Leu
1               5                   10                  15

Ala Ser Glu Ser Arg
            20

<210> SEQ ID NO 54
<211> LENGTH: 21
<212> TYPE: PRT
<213> ORGANISM: Artificial
<220> FEATURE:
<223> OTHER INFORMATION: synthesized

<400> SEQUENCE: 54

Ser Arg Gly Gly Glu Ala Ala Ala Gly Ala Trp Val Ser Phe Ser Ala
1               5                   10                  15

Leu Glu Ser Ser Arg
            20

<210> SEQ ID NO 55
<211> LENGTH: 21
<212> TYPE: PRT
<213> ORGANISM: Artificial
<220> FEATURE:
<223> OTHER INFORMATION: synthesized

<400> SEQUENCE: 55

Ser Arg Val Ser Gly Val Ala Ala Trp Glu Ala Phe Ala Gly Leu Ser
1               5                   10                  15

Val Ser Ser Ser Arg
            20

<210> SEQ ID NO 56
<211> LENGTH: 21
<212> TYPE: PRT
<213> ORGANISM: Artificial
<220> FEATURE:
<223> OTHER INFORMATION: synthesized

<400> SEQUENCE: 56

Ser Arg Asp Gly Gly Ser Phe Ser Ala Phe Ser Ser Leu Val Trp Ala
1               5                   10                  15

Ala Asp Ser Ser Arg
            20

<210> SEQ ID NO 57
<211> LENGTH: 21
<212> TYPE: PRT
<213> ORGANISM: Artificial
<220> FEATURE:
<223> OTHER INFORMATION: synthesized
```

```
<400> SEQUENCE: 57

Ser Ser Val Ala Gly Asp Val Gly Ser Ser Trp Ala Ala Phe Ala Ser
1               5                   10                  15

Leu Ala Ala Ser Arg
            20

<210> SEQ ID NO 58
<211> LENGTH: 21
<212> TYPE: PRT
<213> ORGANISM: Artificial
<220> FEATURE:
<223> OTHER INFORMATION: synthesized

<400> SEQUENCE: 58

Ser Ser Trp Glu Val Phe Ser Ser Leu Glu Ser Gly Ser Val Gly Ala
1               5                   10                  15

Gly Ala Gly Ser Arg
            20

<210> SEQ ID NO 59
<211> LENGTH: 21
<212> TYPE: PRT
<213> ORGANISM: Artificial
<220> FEATURE:
<223> OTHER INFORMATION: synthesized

<400> SEQUENCE: 59

Ser Ser Ser Ser Gly Ala Val Ser Ser Phe Glu Ser Leu Ser Gly Ser
1               5                   10                  15

Val Val Ser Ser Arg
            20

<210> SEQ ID NO 60
<211> LENGTH: 21
<212> TYPE: PRT
<213> ORGANISM: Artificial
<220> FEATURE:
<223> OTHER INFORMATION: synthesized

<400> SEQUENCE: 60

Ser Arg Glu Gly Val Ala Trp Glu Ala Phe Gly Ala Leu Ser Ser Phe
1               5                   10                  15

Ala Ala Asp Ser Arg
            20

<210> SEQ ID NO 61
<211> LENGTH: 21
<212> TYPE: PRT
<213> ORGANISM: Artificial
<220> FEATURE:
<223> OTHER INFORMATION: synthesized

<400> SEQUENCE: 61

Ser Ser Trp Gly Leu Ala Ser Glu Ala Ser Phe Phe Ser Phe Ser Ala
1               5                   10                  15

Leu Ser Ser Ser Arg
            20

<210> SEQ ID NO 62
<211> LENGTH: 21
<212> TYPE: PRT
<213> ORGANISM: Artificial
<220> FEATURE:
<223> OTHER INFORMATION: synthesized
```

```
<400> SEQUENCE: 62

Ser Arg Glu Gly Ala Ala Trp Asp Ser Phe Phe Ala Leu Ser Gly Gly
1               5                   10                  15

Ser Ala Ala Ser Arg
            20

<210> SEQ ID NO 63
<211> LENGTH: 21
<212> TYPE: PRT
<213> ORGANISM: Artificial
<220> FEATURE:
<223> OTHER INFORMATION: synthesized

<400> SEQUENCE: 63

Ser Ser Ala Pro Leu Thr Glu Ser Glu Ala Trp Arg Gly Phe Ser Lys
1               5                   10                  15

Leu Glu Val Ser Arg
            20

<210> SEQ ID NO 64
<211> LENGTH: 21
<212> TYPE: PRT
<213> ORGANISM: Artificial
<220> FEATURE:
<223> OTHER INFORMATION: synthesized

<400> SEQUENCE: 64

Ser Ser Ser Met Pro Val Gly Trp Asp Ser Trp Arg Gly Leu Glu Trp
1               5                   10                  15

Ser Asp Arg Ser Arg
            20

<210> SEQ ID NO 65
<211> LENGTH: 21
<212> TYPE: PRT
<213> ORGANISM: Artificial
<220> FEATURE:
<223> OTHER INFORMATION: synthesized

<400> SEQUENCE: 65

Ser Ser Glu Gly Arg Gly Gly Trp Asn Ser Trp Glu Ala Phe Arg Glu
1               5                   10                  15

Leu Val Val Ser Arg
            20

<210> SEQ ID NO 66
<211> LENGTH: 21
<212> TYPE: PRT
<213> ORGANISM: Artificial
<220> FEATURE:
<223> OTHER INFORMATION: synthesized

<400> SEQUENCE: 66

Ser Ser Gly Gly Gly Gly Ala Trp Glu Ser Trp Arg Gly Leu Ser Gly
1               5                   10                  15

Val Glu Leu Ser Arg
            20

<210> SEQ ID NO 67
<211> LENGTH: 21
<212> TYPE: PRT
<213> ORGANISM: Artificial
<220> FEATURE:
<223> OTHER INFORMATION: synthesized
```

-continued

```
<400> SEQUENCE: 67

Ser Arg Asn Val Glu Gly Ser Trp Glu Ser Phe Ala Gly Leu Ser His
1               5                   10                  15

Val Arg Glu Ser Arg
            20

<210> SEQ ID NO 68
<211> LENGTH: 21
<212> TYPE: PRT
<213> ORGANISM: Artificial
<220> FEATURE:
<223> OTHER INFORMATION: synthesized

<400> SEQUENCE: 68

Ser Arg Glu Asp Gly Gly Arg Trp Glu Ser Phe Leu Gly Leu Ser Ala
1               5                   10                  15

Val Glu Val Ser Arg
            20

<210> SEQ ID NO 69
<211> LENGTH: 21
<212> TYPE: PRT
<213> ORGANISM: Artificial
<220> FEATURE:
<223> OTHER INFORMATION: synthesized

<400> SEQUENCE: 69

Ser Ser Val Glu Gly Ser Ala Trp Ser Ala Phe Lys Ser Leu Ser Ser
1               5                   10                  15

Glu Gly Val Ser Arg
            20

<210> SEQ ID NO 70
<211> LENGTH: 21
<212> TYPE: PRT
<213> ORGANISM: Artificial
<220> FEATURE:
<223> OTHER INFORMATION: synthesized

<400> SEQUENCE: 70

Ser Arg Val Glu Gly Gly Ala Trp Gln Ala Leu Ala Gly Leu Thr Val
1               5                   10                  15

Glu Arg Val Ser Arg
            20

<210> SEQ ID NO 71
<211> LENGTH: 21
<212> TYPE: PRT
<213> ORGANISM: Artificial
<220> FEATURE:
<223> OTHER INFORMATION: synthesized

<400> SEQUENCE: 71

Ser Ser Pro Pro Lys His Ala Trp Gly Ser Phe Asp Ala Leu Gly Gly
1               5                   10                  15

Gln Val Val Ser Arg
            20

<210> SEQ ID NO 72
<211> LENGTH: 21
<212> TYPE: PRT
<213> ORGANISM: Artificial
<220> FEATURE:
<223> OTHER INFORMATION: synthesized
```

-continued

```
<400> SEQUENCE: 72

Ser Ser Glu Arg Gly Val Gly Trp Glu Val Phe Leu Ala Met Glu Gly
1               5                   10                  15

Ala Arg Met Ser Arg
            20

<210> SEQ ID NO 73
<211> LENGTH: 21
<212> TYPE: PRT
<213> ORGANISM: Artificial
<220> FEATURE:
<223> OTHER INFORMATION: synthesized

<400> SEQUENCE: 73

Ser Ser Ser Ser Ser Gly Thr Trp Gln Ala Phe Thr Gly Leu Ser Gly
1               5                   10                  15

Glu Arg Val Ser Arg
            20

<210> SEQ ID NO 74
<211> LENGTH: 21
<212> TYPE: PRT
<213> ORGANISM: Artificial
<220> FEATURE:
<223> OTHER INFORMATION: synthesized

<400> SEQUENCE: 74

Ser Ser Ser Pro Gly Gly Gly Ser Gly Gly Trp Asp Ala Phe Tyr Ser
1               5                   10                  15

Leu Val Gly Ser Arg
            20

<210> SEQ ID NO 75
<211> LENGTH: 21
<212> TYPE: PRT
<213> ORGANISM: Artificial
<220> FEATURE:
<223> OTHER INFORMATION: synthesized

<400> SEQUENCE: 75

Ser Ser Gly Gly Gly Gly Gly Glu Gly Phe Ser Ser Leu Ser Gly
1               5                   10                  15

Asn Gly Arg Ser Arg
            20

<210> SEQ ID NO 76
<211> LENGTH: 21
<212> TYPE: PRT
<213> ORGANISM: Artificial
<220> FEATURE:
<223> OTHER INFORMATION: synthesized

<400> SEQUENCE: 76

Ser Ser Thr Gly Gly Gly Ser Trp Glu Glu Phe Lys Ala Met Thr Pro
1               5                   10                  15

Ser Trp Thr Ser Arg
            20

<210> SEQ ID NO 77
<211> LENGTH: 21
<212> TYPE: PRT
<213> ORGANISM: Artificial
<220> FEATURE:
<223> OTHER INFORMATION: synthesized
```

-continued

```
<400> SEQUENCE: 77

Ser Ser Glu Gly Ser Gly Leu Trp Asp Ser Phe Ser Ser Leu Ser Val
1               5                   10                  15

His Glu Val Ser Arg
            20

<210> SEQ ID NO 78
<211> LENGTH: 21
<212> TYPE: PRT
<213> ORGANISM: Artificial
<220> FEATURE:
<223> OTHER INFORMATION: synthesized

<400> SEQUENCE: 78

Ser Ser Gly Val Thr Gln Glu Ser Ala Ser Trp Ser Ser Phe Arg Thr
1               5                   10                  15

Leu Ala Val Ser Arg
            20

<210> SEQ ID NO 79
<211> LENGTH: 21
<212> TYPE: PRT
<213> ORGANISM: Artificial
<220> FEATURE:
<223> OTHER INFORMATION: synthesized

<400> SEQUENCE: 79

Ser Ser Ser Lys Val Ala Pro Ser Gly Glu Trp Arg Ser Phe Ala Thr
1               5                   10                  15

Leu Glu Val Ser Arg
            20

<210> SEQ ID NO 80
<211> LENGTH: 21
<212> TYPE: PRT
<213> ORGANISM: Artificial
<220> FEATURE:
<223> OTHER INFORMATION: synthesized

<400> SEQUENCE: 80

Ser Ser Glu Ala Gly Arg Gly Trp Glu Gly Phe Lys Ala Leu Glu Gly
1               5                   10                  15

Tyr Gln Val Ser Arg
            20

<210> SEQ ID NO 81
<211> LENGTH: 21
<212> TYPE: PRT
<213> ORGANISM: Artificial
<220> FEATURE:
<223> OTHER INFORMATION: synthesized

<400> SEQUENCE: 81

Ser Ser Leu Gly Gln Thr Gly Trp Glu Ala Phe Glu Ser Leu Ser Gly
1               5                   10                  15

Thr Arg Gly Ser Arg
            20

<210> SEQ ID NO 82
<211> LENGTH: 21
<212> TYPE: PRT
<213> ORGANISM: Artificial
<220> FEATURE:
<223> OTHER INFORMATION: synthesized
```

```
<400> SEQUENCE: 82

Ser Ser Val Ala Trp Asp Ala Phe Thr Val Phe Glu Ser Leu Glu Gly
1               5                   10                  15

Val Ala Thr Ser Arg
            20

<210> SEQ ID NO 83
<211> LENGTH: 21
<212> TYPE: PRT
<213> ORGANISM: Artificial
<220> FEATURE:
<223> OTHER INFORMATION: synthesized

<400> SEQUENCE: 83

Ser Ser Glu Val Val Glu Pro Trp Glu Trp Val Ala Leu Glu Arg
1               5                   10                  15

Ala Gly Gly Ser Arg
            20

<210> SEQ ID NO 84
<211> LENGTH: 21
<212> TYPE: PRT
<213> ORGANISM: Artificial
<220> FEATURE:
<223> OTHER INFORMATION: synthesized

<400> SEQUENCE: 84

Ser Arg Val Ala Ala Val Ser Trp Glu Phe Phe Gly Ser Leu Ser Ser
1               5                   10                  15

Ala Gly Val Ser Arg
            20

<210> SEQ ID NO 85
<211> LENGTH: 21
<212> TYPE: PRT
<213> ORGANISM: Artificial
<220> FEATURE:
<223> OTHER INFORMATION: synthesized

<400> SEQUENCE: 85

Ser Ser Ala Asp Leu Gly Val Ser Gly Ser Trp Glu Gly Phe Ala Leu
1               5                   10                  15

Met Arg Gly Ser Arg
            20

<210> SEQ ID NO 86
<211> LENGTH: 21
<212> TYPE: PRT
<213> ORGANISM: Artificial
<220> FEATURE:
<223> OTHER INFORMATION: synthesized

<400> SEQUENCE: 86

Ser Ser Val Gly Gln Met Gly Trp Glu Ala Phe Glu Ser Leu Ser Gly
1               5                   10                  15

Thr Gly Gly Ser Arg
            20

<210> SEQ ID NO 87
<211> LENGTH: 21
<212> TYPE: PRT
<213> ORGANISM: Artificial
<220> FEATURE:
<223> OTHER INFORMATION: synthesized
```

```
<400> SEQUENCE: 87

Ser Ser Gly Gln Gly Glu Thr Trp Glu Trp Phe Ala Gly Met Arg Gly
1               5                   10                  15

Ser Val Ala Ser Arg
            20

<210> SEQ ID NO 88
<211> LENGTH: 21
<212> TYPE: PRT
<213> ORGANISM: Artificial
<220> FEATURE:
<223> OTHER INFORMATION: synthesized

<400> SEQUENCE: 88

Ser Ser Tyr Phe Asp Val Phe Ser Ser Met Thr Gly Thr Arg Ala Ala
1               5                   10                  15

Gly Ser Trp Ser Arg
            20

<210> SEQ ID NO 89
<211> LENGTH: 21
<212> TYPE: PRT
<213> ORGANISM: Artificial
<220> FEATURE:
<223> OTHER INFORMATION: synthesized

<400> SEQUENCE: 89

Ser Ser Ala Tyr Ser Val Phe Ser Ser Leu Arg Ala Asp Asn Ser Gly
1               5                   10                  15

Gly Ala Val Ser Arg
            20

<210> SEQ ID NO 90
<211> LENGTH: 19
<212> TYPE: PRT
<213> ORGANISM: Artificial
<220> FEATURE:
<223> OTHER INFORMATION: synthesized

<400> SEQUENCE: 90

Ser Ser Gly Gly Ile Ala Ser Leu Lys Tyr Asp Val Val Lys Thr Trp
1               5                   10                  15

Glu Ser Arg

<210> SEQ ID NO 91
<211> LENGTH: 16
<212> TYPE: PRT
<213> ORGANISM: Artificial
<220> FEATURE:
<223> OTHER INFORMATION: synthesized

<400> SEQUENCE: 91

Gly Gly Gly Ala Trp Glu Ala Phe Ser Ser Leu Ser Gly Ser Arg Val
1               5                   10                  15

<210> SEQ ID NO 92
<211> LENGTH: 7
<212> TYPE: PRT
<213> ORGANISM: Artificial
<220> FEATURE:
<223> OTHER INFORMATION: synthesized
<220> FEATURE:
<221> NAME/KEY: MISC_FEATURE
<222> LOCATION: (1)..(1)
<223> OTHER INFORMATION: Xaa is Leu or Val
```

```
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (6)..(6)
<223> OTHER INFORMATION: Xaa is Lys or Arg

<400> SEQUENCE: 92

Xaa Xaa Phe Pro Leu Xaa Gly
1               5

<210> SEQ ID NO 93
<211> LENGTH: 17
<212> TYPE: PRT
<213> ORGANISM: Artificial
<220> FEATURE:
<223> OTHER INFORMATION: synthesized

<400> SEQUENCE: 93

Ser Ser Ser Val Asp Leu Tyr Phe Pro Leu Lys Gly Asp Val Val Ser
1               5                   10                  15

Arg

<210> SEQ ID NO 94
<211> LENGTH: 17
<212> TYPE: PRT
<213> ORGANISM: Artificial
<220> FEATURE:
<223> OTHER INFORMATION: synthesized

<400> SEQUENCE: 94

Ser Ser Phe Glu Pro Leu Arg Phe Pro Leu Lys Gly Val Pro Val Ser
1               5                   10                  15

Arg

<210> SEQ ID NO 95
<211> LENGTH: 21
<212> TYPE: PRT
<213> ORGANISM: Artificial
<220> FEATURE:
<223> OTHER INFORMATION: synthesized

<400> SEQUENCE: 95

Ser Ser Glu Gly Val Gly Gly Phe Pro Leu Lys Gly Ile Pro Gln Glu
1               5                   10                  15

Ala Trp Ala Ser Arg
            20

<210> SEQ ID NO 96
<211> LENGTH: 21
<212> TYPE: PRT
<213> ORGANISM: Artificial
<220> FEATURE:
<223> OTHER INFORMATION: synthesized
<220> FEATURE:
<221> NAME/KEY: MISC_FEATURE
<222> LOCATION: (18)..(18)
<223> OTHER INFORMATION: Xaa is any amino acid

<400> SEQUENCE: 96

Ser Ser Pro Ser Gly Val Val Phe Pro Leu Arg Gly Glu Leu Leu Gly
1               5                   10                  15

Val Xaa Lys Ser Arg
            20
```

```
<210> SEQ ID NO 97
<211> LENGTH: 21
<212> TYPE: PRT
<213> ORGANISM: Artificial
<220> FEATURE:
<223> OTHER INFORMATION: synthesized

<400> SEQUENCE: 97

Ser Ser Gly Gly Phe Val Pro Phe Pro Leu Arg Gly Glu Val Trp Asp
1               5                   10                  15

Gly Val His Ser Arg
            20

<210> SEQ ID NO 98
<211> LENGTH: 21
<212> TYPE: PRT
<213> ORGANISM: Artificial
<220> FEATURE:
<223> OTHER INFORMATION: synthesized

<400> SEQUENCE: 98

Ser Ser Glu Gly Ser Leu Ser Phe Pro Leu Lys Gly Gln Val Tyr Ser
1               5                   10                  15

Gly Trp Gly Ser Arg
            20

<210> SEQ ID NO 99
<211> LENGTH: 21
<212> TYPE: PRT
<213> ORGANISM: Artificial
<220> FEATURE:
<223> OTHER INFORMATION: synthesized

<400> SEQUENCE: 99

Ser Ser Gly Lys Pro Leu Glu Phe Pro Leu Arg Gly Thr Leu Ala Glu
1               5                   10                  15

Trp Pro Val Ser Arg
            20

<210> SEQ ID NO 100
<211> LENGTH: 21
<212> TYPE: PRT
<213> ORGANISM: Artificial
<220> FEATURE:
<223> OTHER INFORMATION: synthesized

<400> SEQUENCE: 100

Ser Arg Gly Glu Ala Leu Gly Phe Pro Leu Thr Gly Gln Leu Met Glu
1               5                   10                  15

Ala Ala Glu Ser Arg
            20

<210> SEQ ID NO 101
<211> LENGTH: 21
<212> TYPE: PRT
<213> ORGANISM: Artificial
<220> FEATURE:
<223> OTHER INFORMATION: synthesized

<400> SEQUENCE: 101

Ser Ser Met Trp Asp Val Gly Phe Pro Leu Lys Gly Arg Trp Ile Asp
1               5                   10                  15

Gly Ala Asp Ser Arg
            20
```

```
<210> SEQ ID NO 102
<211> LENGTH: 21
<212> TYPE: PRT
<213> ORGANISM: Artificial
<220> FEATURE:
<223> OTHER INFORMATION: synthesized

<400> SEQUENCE: 102

Ser Ser Ser Asn Ser Leu Trp Phe Pro Leu Arg Gly Ser Thr Val Glu
1               5                   10                  15

Val Gly Ala Ser Arg
            20

<210> SEQ ID NO 103
<211> LENGTH: 21
<212> TYPE: PRT
<213> ORGANISM: Artificial
<220> FEATURE:
<223> OTHER INFORMATION: synthesized

<400> SEQUENCE: 103

Ser Ser Gly Pro Ala Leu Arg Leu Pro Leu Arg Gly Thr Val Val Ser
1               5                   10                  15

Asp Val Pro Ser Arg
            20

<210> SEQ ID NO 104
<211> LENGTH: 21
<212> TYPE: PRT
<213> ORGANISM: Artificial
<220> FEATURE:
<223> OTHER INFORMATION: synthesized

<400> SEQUENCE: 104

Ser Ser Ala Asp Arg Val Ala Trp Pro Leu Lys Gly Ala Pro Val Trp
1               5                   10                  15

Val Lys Glu Ser Arg
            20

<210> SEQ ID NO 105
<211> LENGTH: 21
<212> TYPE: PRT
<213> ORGANISM: Artificial
<220> FEATURE:
<223> OTHER INFORMATION: synthesized

<400> SEQUENCE: 105

Ser Ser Gly Leu Ala Leu Gly Leu Pro Ile Lys Gly Trp Thr Val Ser
1               5                   10                  15

Gly Lys Asp Ser Arg
            20

<210> SEQ ID NO 106
<211> LENGTH: 21
<212> TYPE: PRT
<213> ORGANISM: Artificial
<220> FEATURE:
<223> OTHER INFORMATION: synthesized

<400> SEQUENCE: 106

Ser Ser Gly Tyr Thr Leu Gly Phe Pro Leu Ser Gly Gln Thr Ile Lys
1               5                   10                  15

Asp Trp Pro Ser Arg
            20
```

```
<210> SEQ ID NO 107
<211> LENGTH: 21
<212> TYPE: PRT
<213> ORGANISM: Artificial
<220> FEATURE:
<223> OTHER INFORMATION: synthesized

<400> SEQUENCE: 107

Ser Ser Glu Gly Trp Val His Phe Pro Leu Lys Gly Asp Val Met Gly
1               5                   10                  15

Gly Pro Phe Ser Arg
            20

<210> SEQ ID NO 108
<211> LENGTH: 21
<212> TYPE: PRT
<213> ORGANISM: Artificial
<220> FEATURE:
<223> OTHER INFORMATION: synthesized

<400> SEQUENCE: 108

Ser Ser Gly Arg Tyr Val Ser Leu Pro Leu Lys Gly Glu Val Val Pro
1               5                   10                  15

Gln Thr Ala Ser Arg
            20

<210> SEQ ID NO 109
<211> LENGTH: 21
<212> TYPE: PRT
<213> ORGANISM: Artificial
<220> FEATURE:
<223> OTHER INFORMATION: synthesized

<400> SEQUENCE: 109

Ser Ser Glu Gly Gly Val Gly Phe Pro Leu Lys Gly Ile Pro Gln Glu
1               5                   10                  15

Ala Trp Ala Ser Arg
            20

<210> SEQ ID NO 110
<211> LENGTH: 21
<212> TYPE: PRT
<213> ORGANISM: Artificial
<220> FEATURE:
<223> OTHER INFORMATION: synthesized

<400> SEQUENCE: 110

Ser Arg Val Asp Ser Val Asn Phe Pro Leu Arg Gly Glu Thr Val Thr
1               5                   10                  15

Ser Met Val Ser Arg
            20

<210> SEQ ID NO 111
<211> LENGTH: 21
<212> TYPE: PRT
<213> ORGANISM: Artificial
<220> FEATURE:
<223> OTHER INFORMATION: synthesized

<400> SEQUENCE: 111

Ser Ser Glu Gly Val Gly Gly Phe Pro Leu Lys Gly Ile Pro Gln Glu
1               5                   10                  15

Ala Trp Ala Ser Arg
            20
```

```
<210> SEQ ID NO 112
<211> LENGTH: 21
<212> TYPE: PRT
<213> ORGANISM: Artificial
<220> FEATURE:
<223> OTHER INFORMATION: synthesized
<220> FEATURE:
<221> NAME/KEY: MISC_FEATURE
<222> LOCATION: (18)..(18)
<223> OTHER INFORMATION: Xaa is any amino acid

<400> SEQUENCE: 112

Ser Ser Pro Ser Gly Val Val Phe Pro Leu Arg Gly Glu Leu Leu Gly
1               5                   10                  15

Val Xaa Lys Ser Arg
            20

<210> SEQ ID NO 113
<211> LENGTH: 21
<212> TYPE: PRT
<213> ORGANISM: Artificial
<220> FEATURE:
<223> OTHER INFORMATION: synthesized

<400> SEQUENCE: 113

Ser Ser Gly Gly Phe Val Pro Phe Pro Leu Arg Gly Glu Val Trp Asp
1               5                   10                  15

Gly Val His Ser Arg
            20

<210> SEQ ID NO 114
<211> LENGTH: 21
<212> TYPE: PRT
<213> ORGANISM: Artificial
<220> FEATURE:
<223> OTHER INFORMATION: synthesized

<400> SEQUENCE: 114

Ser Ser Glu Gly Ser Leu Ser Phe Pro Leu Lys Gly Gln Val Tyr Ser
1               5                   10                  15

Gly Trp Gly Ser Arg
            20

<210> SEQ ID NO 115
<211> LENGTH: 21
<212> TYPE: PRT
<213> ORGANISM: Artificial
<220> FEATURE:
<223> OTHER INFORMATION: synthesized

<400> SEQUENCE: 115

Ser Ser Gly Lys Pro Leu Glu Phe Pro Leu Arg Gly Thr Leu Ala Glu
1               5                   10                  15

Trp Pro Val Ser Arg
            20

<210> SEQ ID NO 116
<211> LENGTH: 21
<212> TYPE: PRT
<213> ORGANISM: Artificial
<220> FEATURE:
<223> OTHER INFORMATION: synthesized
```

<400> SEQUENCE: 116

Ser Arg Gly Glu Ala Leu Gly Phe Pro Leu Thr Gly Gln Leu Met Glu
1               5                   10                  15

Ala Ala Glu Ser Arg
            20

<210> SEQ ID NO 117
<211> LENGTH: 21
<212> TYPE: PRT
<213> ORGANISM: Artificial
<220> FEATURE:
<223> OTHER INFORMATION: synthesized

<400> SEQUENCE: 117

Ser Ser Met Trp Asp Val Gly Phe Pro Leu Lys Gly Arg Trp Ile Asp
1               5                   10                  15

Gly Ala Asp Ser Arg
            20

<210> SEQ ID NO 118
<211> LENGTH: 17
<212> TYPE: PRT
<213> ORGANISM: Artificial
<220> FEATURE:
<223> OTHER INFORMATION: synthesized

<400> SEQUENCE: 118

Gly Gly Ala Leu Gly Phe Pro Leu Lys Gly Glu Val Val Glu Gly Trp
1               5                   10                  15

Ala

<210> SEQ ID NO 119
<211> LENGTH: 4
<212> TYPE: PRT
<213> ORGANISM: Artificial
<220> FEATURE:
<223> OTHER INFORMATION: synthesized
<220> FEATURE:
<221> NAME/KEY: MISC_FEATURE
<222> LOCATION: (4)..(4)
<223> OTHER INFORMATION: Xaa is any amino acid

<400> SEQUENCE: 119

Arg Gly Asp Xaa
1

<210> SEQ ID NO 120
<211> LENGTH: 12
<212> TYPE: PRT
<213> ORGANISM: Artificial
<220> FEATURE:
<223> OTHER INFORMATION: synthesized

<400> SEQUENCE: 120

Ala Leu Pro Ser Thr Ser Ser Gln Met Pro Gln Leu
1               5                   10

<210> SEQ ID NO 121
<211> LENGTH: 23
<212> TYPE: PRT
<213> ORGANISM: Artificial
<220> FEATURE:
<223> OTHER INFORMATION: synthesized

<400> SEQUENCE: 121

Ser Ser Ser Cys Gln His Val Ser Leu Leu Arg Pro Ser Ala Ala Leu
1               5                   10                  15

Gly Pro Asp Asn Cys Ser Arg
            20

<210> SEQ ID NO 122
<211> LENGTH: 27
<212> TYPE: PRT
<213> ORGANISM: Artificial
<220> FEATURE:
<223> OTHER INFORMATION: synthesized

<400> SEQUENCE: 122

Leu Glu Arg Gly Arg Asp Tyr Glu Lys Asn Lys Val Cys Lys Glu Phe
1               5                   10                  15

Ser His Leu Gly Lys Asp Asp Phe Glu Asp Phe
            20                  25

<210> SEQ ID NO 123
<211> LENGTH: 12
<212> TYPE: PRT
<213> ORGANISM: Artificial
<220> FEATURE:
<223> OTHER INFORMATION: synthesized

<400> SEQUENCE: 123

His Thr Pro His Pro Asp Ala Ser Ile Gln Gly Val
1               5                   10

<210> SEQ ID NO 124
<211> LENGTH: 4
<212> TYPE: PRT
<213> ORGANISM: Artificial
<220> FEATURE:
<223> OTHER INFORMATION: synthesized

<400> SEQUENCE: 124

Val Met Asn Val
1

<210> SEQ ID NO 125
<211> LENGTH: 4
<212> TYPE: PRT
<213> ORGANISM: Artificial
<220> FEATURE:
<223> OTHER INFORMATION: synthesized

<400> SEQUENCE: 125

Ala Glu Asp Gly
1

<210> SEQ ID NO 126
<211> LENGTH: 48
<212> TYPE: DNA
<213> ORGANISM: Artificial
<220> FEATURE:
<223> OTHER INFORMATION: synthesized

<400> SEQUENCE: 126
agcatttttt ctacttggaa tccgtggtcg ccttattctg tgtctaga                48

<210> SEQ ID NO 127
<211> LENGTH: 45
<212> TYPE: DNA
<213> ORGANISM: Artificial

```
<220> FEATURE:
<223> OTHER INFORMATION: synthesized

<400> SEQUENCE: 127
agttttgggt cgtggtggtg ggggtctggt gctgcttcgt ctaga                  45

<210> SEQ ID NO 128
<211> LENGTH: 60
<212> TYPE: DNA
<213> ORGANISM: Artificial
<220> FEATURE:
<223> OTHER INFORMATION: synthesized

<400> SEQUENCE: 128
agttgggatt ttcgttcttt gcgtgactgg tggcctccgg ctccttcttt gtcgtctaga   60

<210> SEQ ID NO 129
<211> LENGTH: 48
<212> TYPE: DNA
<213> ORGANISM: Artificial
<220> FEATURE:
<223> OTHER INFORMATION: synthesized

<400> SEQUENCE: 129
agctttgata ttgattggtc tggtatgcgt tcgtggtggg ggtctaga               48

<210> SEQ ID NO 130
<211> LENGTH: 48
<212> TYPE: DNA
<213> ORGANISM: Artificial
<220> FEATURE:
<223> OTHER INFORMATION: synthesized

<400> SEQUENCE: 130
agctggtggg gtttttggaa tggttcggcg gcgcctgtgt ggtctaga               48

<210> SEQ ID NO 131
<211> LENGTH: 60
<212> TYPE: DNA
<213> ORGANISM: Artificial
<220> FEATURE:
<223> OTHER INFORMATION: synthesized

<400> SEQUENCE: 131
agtcttggga cgttttggtc ttcggtgtgg cggggcgtgg atgcgggtgg tgagtctaga   60

<210> SEQ ID NO 132
<211> LENGTH: 48
<212> TYPE: DNA
<213> ORGANISM: Artificial
<220> FEATURE:
<223> OTHER INFORMATION: synthesized

<400> SEQUENCE: 132
agcttttctt ggttttctta tccgtctcag ctgtggatgg agtctaga               48

<210> SEQ ID NO 133
<211> LENGTH: 36
<212> TYPE: PRT
<213> ORGANISM: Artificial
<220> FEATURE:
<223> OTHER INFORMATION: synthesized
```

<400> SEQUENCE: 133

Ser Trp Trp Gly Phe Trp Asn Gly Ser Ala Ala Pro Val Trp Ser Arg
1               5                   10                  15

Gly Ser Ser Glu Ser Ala Gly Ala Trp Glu Ala Phe Ser Ser Leu Ser
            20                  25                  30

Gly Ser Arg Val
        35

<210> SEQ ID NO 134
<211> LENGTH: 35
<212> TYPE: PRT
<213> ORGANISM: Artificial
<220> FEATURE:
<223> OTHER INFORMATION: synthesized

<400> SEQUENCE: 134

Ser Trp Trp Gly Phe Trp Asn Gly Ser Ala Ala Pro Val Trp Ser Arg
1               5                   10                  15

Gly Ser Ser Gly Ala Gly Ala Trp Glu Ala Phe Ser Ser Leu Ser Gly
            20                  25                  30

Ser Arg Val
        35

<210> SEQ ID NO 135
<211> LENGTH: 37
<212> TYPE: PRT
<213> ORGANISM: Artificial
<220> FEATURE:
<223> OTHER INFORMATION: synthesized

<400> SEQUENCE: 135

Ser Trp Trp Gly Phe Trp Asn Gly Ser Ala Ala Pro Val Trp Ser Arg
1               5                   10                  15

Gly Ser Ser Gly Ala Gly Ala Leu Gly Phe Pro Leu Lys Gly Glu Val
            20                  25                  30

Val Glu Gly Trp Ala
        35

<210> SEQ ID NO 136
<211> LENGTH: 36
<212> TYPE: PRT
<213> ORGANISM: Artificial
<220> FEATURE:
<223> OTHER INFORMATION: synthesized

<400> SEQUENCE: 136

Ser Phe Gly Ser Trp Trp Gly Ser Gly Ala Ala Ser Ser Arg Gly
1               5                   10                  15

Ser Ser Gly Gly Gly Ala Leu Gly Phe Pro Leu Lys Gly Glu Val Val
            20                  25                  30

Glu Gly Trp Ala
        35

<210> SEQ ID NO 137
<211> LENGTH: 41
<212> TYPE: PRT
<213> ORGANISM: Artificial
<220> FEATURE:
<223> OTHER INFORMATION: synthesized -continued

```
<400> SEQUENCE: 137

Ser Trp Trp Gly Phe Trp Asn Gly Ser Ala Ala Pro Val Trp Ser Arg
1               5                   10                  15

Gly Ser Ser Glu Ser Ala Gly Ala Trp Glu Ala Phe Ser Ser Leu Ser
            20                  25                  30

Gly Ser Arg Val Gly Ser Ser Gly Lys
        35                  40

<210> SEQ ID NO 138
<211> LENGTH: 40
<212> TYPE: PRT
<213> ORGANISM: Artificial
<220> FEATURE:
<223> OTHER INFORMATION: synthesized

<400> SEQUENCE: 138

Ser Trp Trp Gly Phe Trp Asn Gly Ser Ala Ala Pro Val Trp Ser Arg
1               5                   10                  15

Gly Ser Ser Gly Ala Gly Ala Trp Glu Ala Phe Ser Ser Leu Ser Gly
            20                  25                  30

Ser Arg Val Gly Ser Ser Gly Lys
        35                  40

<210> SEQ ID NO 139
<211> LENGTH: 42
<212> TYPE: PRT
<213> ORGANISM: Artificial
<220> FEATURE:
<223> OTHER INFORMATION: synthesized

<400> SEQUENCE: 139

Ser Trp Trp Gly Phe Trp Asn Gly Ser Ala Ala Pro Val Trp Ser Arg
1               5                   10                  15

Gly Ser Ser Gly Ala Gly Ala Leu Gly Phe Pro Leu Lys Gly Glu Val
            20                  25                  30

Val Glu Gly Trp Ala Gly Ser Ser Gly Lys
        35                  40

<210> SEQ ID NO 140
<211> LENGTH: 41
<212> TYPE: PRT
<213> ORGANISM: Artificial
<220> FEATURE:
<223> OTHER INFORMATION: synthesized

<400> SEQUENCE: 140

Ser Phe Gly Ser Trp Trp Gly Ser Gly Ala Ala Ser Ser Arg Gly
1               5                   10                  15

Ser Ser Gly Gly Gly Ala Leu Gly Phe Pro Leu Lys Gly Glu Val Val
            20                  25                  30

Glu Gly Trp Ala Gly Ser Ser Gly Lys
        35                  40

<210> SEQ ID NO 141
<211> LENGTH: 37
<212> TYPE: PRT
<213> ORGANISM: Artificial
<220> FEATURE:
<223> OTHER INFORMATION: synthesized
<220> FEATURE:
<221> NAME/KEY: MISC_FEATURE
<222> LOCATION: (16)..(17)
<223> OTHER INFORMATION: amino acid 16 joined to amino acid 17 via a
      linker
```

-continued

```
<400> SEQUENCE: 141

Ser Phe Gly Ser Trp Trp Trp Gly Ser Gly Ala Ala Ser Ser Arg Gly
1               5                   10                  15

Gly Gly Gly Ala Trp Glu Ala Phe Ser Ser Leu Ser Gly Ser Arg Val
            20                  25                  30

Gly Ser Ser Gly Lys
            35

<210> SEQ ID NO 142
<211> LENGTH: 36
<212> TYPE: PRT
<213> ORGANISM: Artificial
<220> FEATURE:
<223> OTHER INFORMATION: synthesized
<220> FEATURE:
<221> NAME/KEY: MISC_FEATURE
<222> LOCATION: (16)..(17)
<223> OTHER INFORMATION: amino acid 16 joined to amino acid 17 via a
      linker

<400> SEQUENCE: 142

Ser Phe Gly Ser Trp Trp Trp Gly Ser Gly Ala Ala Ser Ser Arg Gly
1               5                   10                  15

Ala Gly Ala Trp Glu Ala Phe Ser Ser Leu Ser Gly Ser Arg Val Gly
            20                  25                  30

Ser Ser Gly Lys
            35
```